US012649898B2

(12) United States Patent
Rittmann et al.

(10) Patent No.: US 12,649,898 B2
(45) Date of Patent: *Jun. 9, 2026

(54) METHOD AND SYSTEM FOR MEMBRANE CARBONATION

(71) Applicant: Arizona Board of Regents on Behalf of Arizona State University, Scottsdale, AZ (US)

(72) Inventors: Bruce Rittmann, Tempe, AZ (US); Everett Eustance, Queen Creek, AZ (US); Yen-Jung Lai, Tempe, AZ (US); Justin Flory, Scottsdale, AZ (US); Diana Calvo Martinez, Phoenix, AZ (US); Tarun Shesh, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/622,737

(22) Filed: Mar. 29, 2024

(65) Prior Publication Data

US 2024/0384216 A1 Nov. 21, 2024

Related U.S. Application Data

(63) Continuation of application No. 16/809,384, filed on Mar. 4, 2020, now Pat. No. 11,970,683.

(60) Provisional application No. 62/814,216, filed on Mar. 5, 2019.

(51) Int. Cl.
*C12M 1/00* (2006.01)
*C12M 1/34* (2006.01)
*C12N 1/12* (2006.01)

(52) U.S. Cl.
CPC ............ *C12M 29/16* (2013.01); *C12M 41/26* (2013.01); *C12N 1/12* (2013.01)

(58) Field of Classification Search
CPC ......... C12N 1/12; C12M 29/06; C12M 21/02; C12M 29/16; C12M 41/26; C12M 23/18
See application file for complete search history.

(56) References Cited

U.S. PATENT DOCUMENTS

| | | | | |
|---|---|---|---|---|
| 9,102,953 B2 * | 8/2015 | Downey | ................. | C12M 21/04 |
| 9,255,472 B2 * | 2/2016 | Downey | ................. | C12M 21/04 |
| 9,938,217 B2 * | 4/2018 | Wright | .................... | C07C 41/01 |
| 2007/0295505 A1 * | 12/2007 | Pfeiffer | ................... | C12P 5/023 |
| | | | | 166/263 |

* cited by examiner

*Primary Examiner* — Shogo Sasaki
(74) *Attorney, Agent, or Firm* — FULLER IP LAW LLC; Rodney J. Fuller

(57) ABSTRACT

Disclosed herein are methods and systems for membrane carbonation for cultivating microalgae and other microorganisms that utilize a gaseous substrate, as well as to upgrade the quality of mixed-gas streams.

6 Claims, 26 Drawing Sheets pH Probe
location

METHOD AND SYSTEM FOR MEMBRANE CARBONATION

CROSS REFERENCE TO RELATED APPLICATION

This application is a continuation of U.S. Utility application Ser. No. 16/809,384, filed on Mar. 4, 2020, which claims the benefit of the earlier filing date of U.S. Provisional Application No. 62/814,216, filed Mar. 5, 2019, which are hereby incorporated by reference in their entirety.

ACKNOWLEDGMENT OF GOVERNMENT SUPPORT

This invention was made with government support under DE-EE0007093 and DE-EE0008517 awarded by the Department of Energy and 1603656 awarded by the National Science Foundation. The government has certain rights in the invention.

FIELD

This disclosure relates to the field of membrane carbonation (MC) and in particular, to methods and systems for membrane carbonation for cultivating microalgae, homoacetogenic bacteria, chain elongating bacteria, and other microorganisms to produce sustainable fuels and other high-value products.

BACKGROUND $CO_2$ delivery is critical to high productivity in algal cultivation. Moreover, it is becoming increasingly important to efficiently deliver $CO_2$ to reduce feedstock costs. As $CO_2$ demand is inconsistent due to varying environmental, seasonal, and nutrient conditions, $CO_2$ delivery mechanisms needs to be efficient and able to handle a broad range of delivery rates. The same situation is present for the delivery of CO, $CH_4$, $NH_3$, $O_2$, $H_2$, and $H_2S$ gases.

SUMMARY

Disclosed herein are methods and systems for membrane carbonation for cultivating photoautotrophic and chemoautotrophic microorganisms, including microalgae and bacteria, to produce sustainable fuels and other products, as well as to upgrade the quality of mixed-gas streams. In some embodiments, a method for membrane carbonation for cultivating a photoautotrophic organism, comprises placing a bundle or sheet of non-porous hollow fibers into a photoautotrophic culture; delivering a mixture of gases including $CO_2$ to the non-porous hollow fibers under conditions sufficient to allow the $CO_2$ to pass through the non-porous hollow fibers and into the photoautotrophic culture; and controlling the mixture of gases including $CO_2$ delivery rate through distal-end non-porous hollow fibers by monitoring photoautotrophic culture pH, thereby improving growth rate and/or biomass productivity and minimizing $CO_2$ lost to the environment. In some embodiments, controlling the mixture of gases delivery rate through distal-end non-porous hollow fibers comprises coupling a solenoid valve to distal end non-porous hollow fibers and purging accumulated water vapor and inert gases from the non-porous hollow fibers to maintain a desired pH of the culture. In embodiments, the method provides bubbleless $CO_2$ transfer. In some embodiments, the photoautotrophic organism is an algae or bacteria.

In some embodiments, the algae is a microalgae. In some embodiments, the algae is selected from the group consisting of microalga *Scenedesmus acutus*, marine coccolithophore algae *Emiliania huxleyi*, marine coccolithophore algae *Chaetoceros gracilis*, and diatom algae *Pleurochrysis carterae*. In some embodiments, the bacteria is a cyanobacteria, such as *Synechocystis* sp. PCC 6803. In some embodiments, the bacteria is homoacetogenic bacteria. In some embodiments, purging accumulated water vapor and inert gases from the non-porous hollow fibers to maintain a desired pH of the culture comprises opening a venting valve for a sufficient amount of time to allow sweep gas to replace existing volume of the non-porous hollow fibers with gas at a concentration equivalent to an inlet gas concentration when a secondary (elevated) pH setpoint is reached which indicates that flux of $CO_2$ through the non-porous hollow fibers is lower than operational demand of the photoautotrophic culture. In some embodiments, the method further comprises providing a relatively constant flow of gas out distal end non-porous hollow fibers when the venting valve at an inlet of the non-porous hollow fibers is opened by use of a bleed valve. In some embodiments, the bleed valve is operated with a pH-controlled solenoid valve and wherein the venting valve at the distal end of the non-porous hollow fibers is controlled by pH setpoint. In some embodiments, the bleed valve is designed for use in <100% $CO_2$ feed gases and is used to restrict the flow to ensure <10% of the $CO_2$ exits the distal end of the non-porous hollow fibers. In some embodiments, the mixed-gas includes a secondary gas that is more valuable when purified to a higher concentration as $CO_2$ is removed. In some embodiments, the photoautotrophic culture comprises microalgae which are co-cultured with an $H_2S$-oxidizing microorganism to remove $CO_2$ and $H_2S$ from (1) biogas to enrich the $CH_4$ content exiting the non-porous hollow fibers or (2) synthesis gas (or syngas) from the gas mixture exiting the non-porous hollow fibers. In some embodiments, the $H_2S$-oxidizing microorganism is Beggiatoaceae, purple sulfur bacteria, green sulfur bacteria, *Acidithiobacillus, Aquaspirillum, Aquifex, Bacillus, Methylobacterium, Paracoccus, Pseudomonas, Starkeya, Thermithiobacillus*, and/or *Xanthobacteria*. In some embodiments, the photoautotrophic culture comprises microalgae and the microalgae is replaced with a CO oxidizing microorganism to remove it from a mixed gas containing CO or $CH_4$ oxidizing microorganism to remove it from a mixed gas containing $CH_4$. In some embodiments, the CO oxidizing microorganism is Oligotropha, Stappia or Mycobacterium and the mixed gas is flue gas from a natural gas, oil, wood, coal or carbon-based fuel combusted in a power plant. In some embodiments, the $CH_4$ oxidizing microorganism is Methylococcaceae, Methylocystaceae, Gammaproteobacteria, or Alphaproteobacteria and the mixed gas is syngas or biogas.

In some embodiments, a system for membrane carbonation for cultivating a photoautotrophic organism comprises a non-porous hollow fiber membranes to deliver mixtures of gases containing $CO_2$ to a photoautotrophic culture; a solenoid valve for providing the mixtures of gases containing $CO_2$ to the non-porous hollow fiber membranes; a pH probe for monitoring pH of the photoautotrophic culture; and a bleed valve for preventing accumulation of inert gasses, while maintaining a pressure similar to fiber inlet thereby ensuring high $CO_2$-transfer efficiency and minimizing the effect of inert gases on $CO_2$ flux rates. In some embodiments, the photoautotrophic organism is algae or bacteria.

In some embodiments, a system for membrane carbonation for producing fatty acids and alcohols comprises non-porous hollow fiber membranes to deliver synthesis gas is disclosed which is composed of hydrogen, carbon monoxide, and carbon dioxide—to an enriched biofilm growing in the outer layer of the fiber; a peristaltic pump to recirculate media; a flushing valve to release $CO_2$ and CO excess inside the lumen; two liquid sampling ports at input and output; and one gas sampling port at output. In some embodiments, the enriched biofilm is mainly acetogens and chain elongators with wasted activated sludge as initial inoculum.

The foregoing and other features of the disclosure will become more apparent from the following detailed description, which proceeds with reference to the accompanying figures.

DETAILED DESCRIPTION OF SEVERAL EMBODIMENTS

The terms "a" and "an" are defined as one or more unless this disclosure explicitly requires otherwise.

The terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, any of the present devices, systems, and methods that "comprises," "has," "includes" or "contains" one or more elements possesses those one or more elements, but is not limited to possessing only those one or more elements. Likewise, an element of a device, system, or method that "comprises," "has," "includes" or "contains" one or more features possesses those one or more features, but is not limited to possessing only those one or more features. Additionally, terms such as "first" and "second" are used only to differentiate structures or features, and not to limit the different structures or features to a particular order.

Furthermore, a structure that is capable performing a function or that is configured in a certain way is capable or configured in at least that way, but may also be capable or configured in ways that are not listed.

The feature or features of one embodiment may be applied to other embodiments, even though not described or illustrated, unless expressly prohibited by this disclosure or the nature of the embodiments.

Any of the present devices, systems, and methods can consist of or consist essentially of rather than comprise/include/contain/have any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Figure 1:
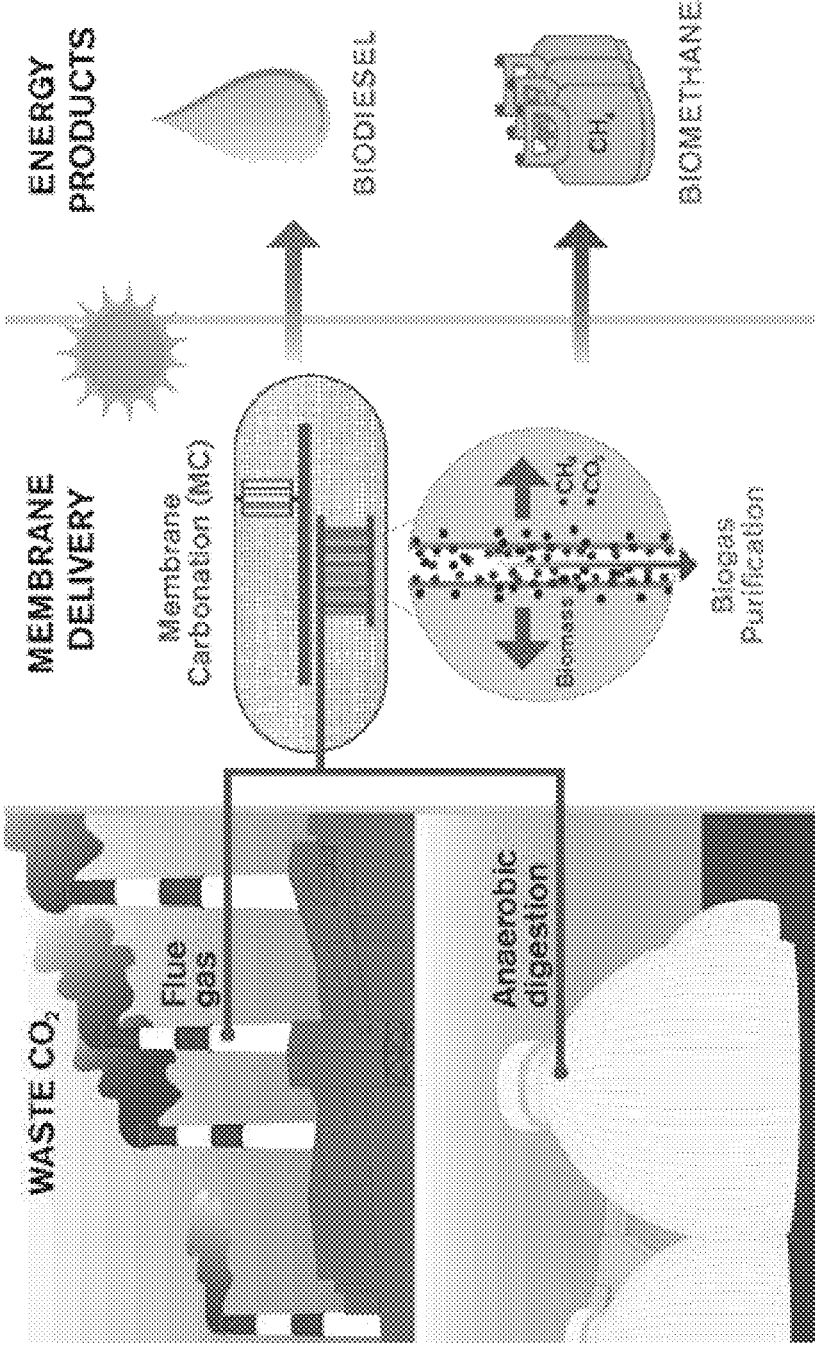
FIG. 1 illustrates membrane carbonation (MC) delivers industrial $CO_2$-containing gas streams to microalgae at ≥90% efficiency by diffusion through hollow-fiber gas-transfer membranes. Microalgal productivity towards biodiesel can be increased greatly and the value of other energy products can be upgraded.

Disclosed herein are methods and systems for membrane carbonation (MC), which utilizes non-porous hollow fiber membranes to deliver $CO_2$ to photoautotrophic cultures, such as algal and cyanobacteria, cultures for high efficiency $CO_2$ transfer. $CO_2$ delivery is used as a mechanism to control pH and to prevent carbon limitation in the culture, both of which are needed to maintain high algal growth rates. Depending on the source and concentration of the $CO_2$ being delivered, the MC system has different operational parameters to maintain high $CO_2$ transfer efficiency while minimizing fiber surface area. In addition to delivering $CO_2$ to the cultures, the technology concentrates other gases that are mixed with the $CO_2$ to improve the product quality and capture at exiting end of the fibers (FIG. 1).

The MC technology of this disclosure focuses on the bubbleless delivery of $CO_2$ into photoautotrophic cultures, such as algal and cyanobacteria cultures, to improve the growth rate and biomass productivity, minimize $CO_2$ lost to the environment, and ensuring the culture maintains a desired pH range. MC is desired as the bubbleless delivery of $CO_2$ via molecular diffusion across a non-porous hollow fiber membrane (HFM) provides a mediated transfer from the gas phase to the liquid phase, which creates 100% transfer efficiency. This can significantly decrease the amount of costly $CO_2$ lost to the environment during photoautotrophic, such as algal and cyanobacteria, cultivation, which decreases the cost of cultivation of the photoautotroph and reduces $CO_2$ emissions.

The disclosed systems and methods are contemplated to be useful for the cultivation of any photoautotrophic organism. Photoautotrophic organisms are organisms that derive their energy for food synthesis from light and are capable of using carbon dioxide as their principal source of carbon. In some embodiments, exemplary photoautotrophic organisms include algae or bacteria, such as microalgae and/or cyanobacteria. In some embodiments, exemplary photoautotrophic organisms include one or more of microalga *Scenedesmus acutus*, marine coccolithophore algae *Emiliania huxleyi*, marine coccolithophore algae *Chaetoceros gracilis*, diatom algae *Pleurochrysis carterae*, cyanobacterium *Synechocystis* sp. PCC 6803, microalgae chlorophytes, euglenophytes, charophytes, diatoms, dinoflagellates, cryptophytes, or xanthophytes, and macroalgae rhodophytes or phaeophytes.

A concept of the disclosure is the efficient delivery of $CO_2$ through non-porous hollow fiber membranes, known as MC. The principle theory is a concentration gradient across the membrane creates a driving force that causes molecular diffusion of $CO_2$ to transfer from the lumen side of the fiber to the surrounding culture medium. This mechanism is affected by several factors: 1) Concentration of $CO_2$ in the lumen; 2) operational pressure inside the fibers; 3) fiber design; and 4) operating conditions/methods. Typically, the pressure of the $CO_2$ in the lumen dictates the operating parameters as described in more detail below. In exemplary embodiments, operating pressures of the fibers are between about 1 and about 150 psig, such as 1 psig, 10 psig, 20 psig, 30 psig, 40 psig, 50 psig, 60 psig, 70 psig, 80 psig, 90 psig, 100 psig, 110 psig, 120 psig, 130 psig, 140 psig or 150 psig to ensure that neither rupture of the fibers nor bubble formation occur. Lower pressures, such as 1-10 psig, are utilized to provide decreased flux values when algal cultures are exhibiting low biomass productivity. This occurs during the winter due to seasonally low temperatures and during cloudy weather that decreases light availability. Fiber designs can use any non-porous material including, but not limited to single layer polypropylene and composite fibers. Composite fibers provide a significant increase in molecular diffusion as the non-porous layer is significantly thinner (approximately 1 micron). This significantly decreases diffusion resistance.

Figure 2:
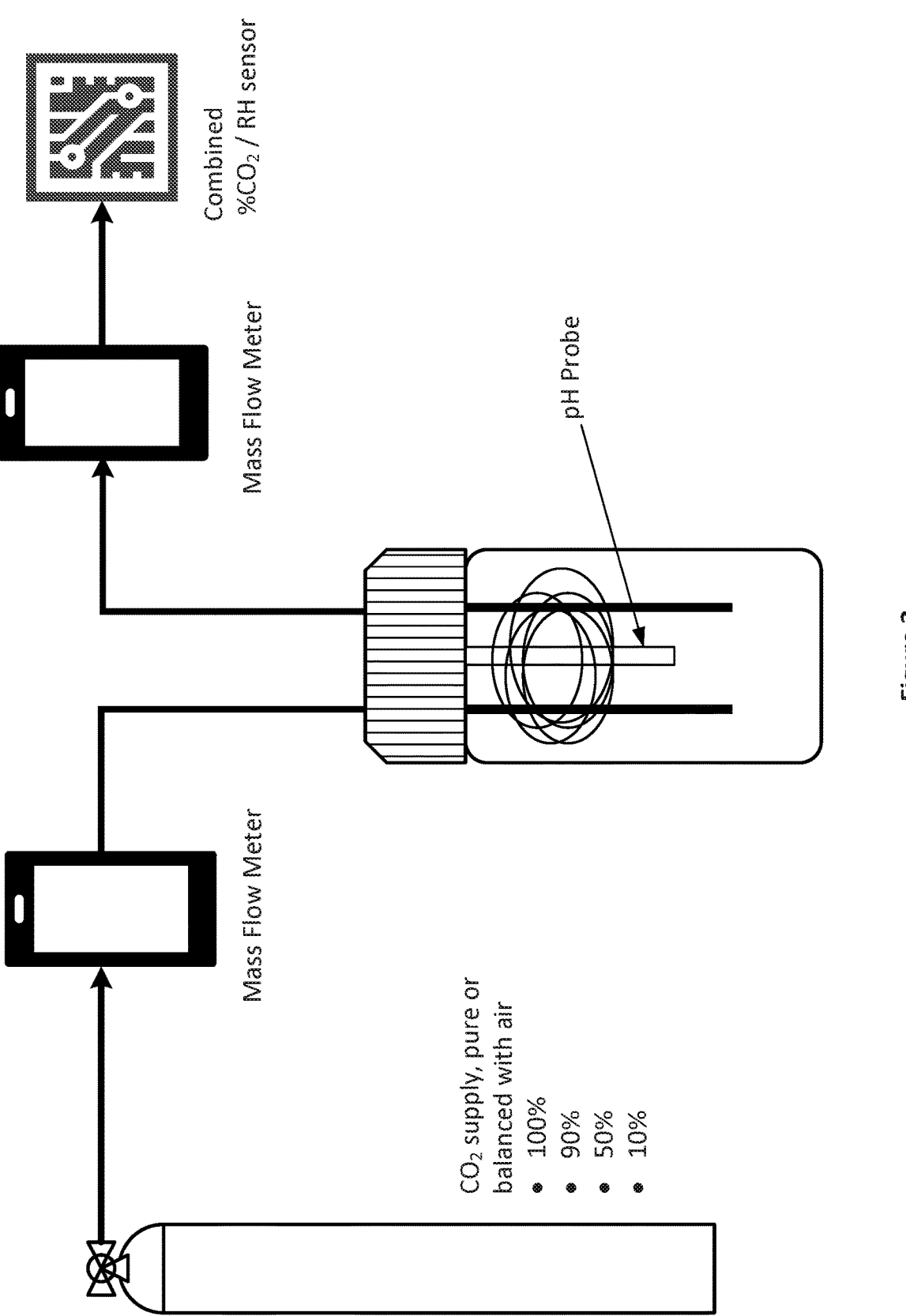
FIG. 2 is a schematic representation of an exemplary setup of indoor culture conditions using flow controllers to manage $CO_2$ delivery in accordance with embodiments described herein.
Figures 3A, 3B:
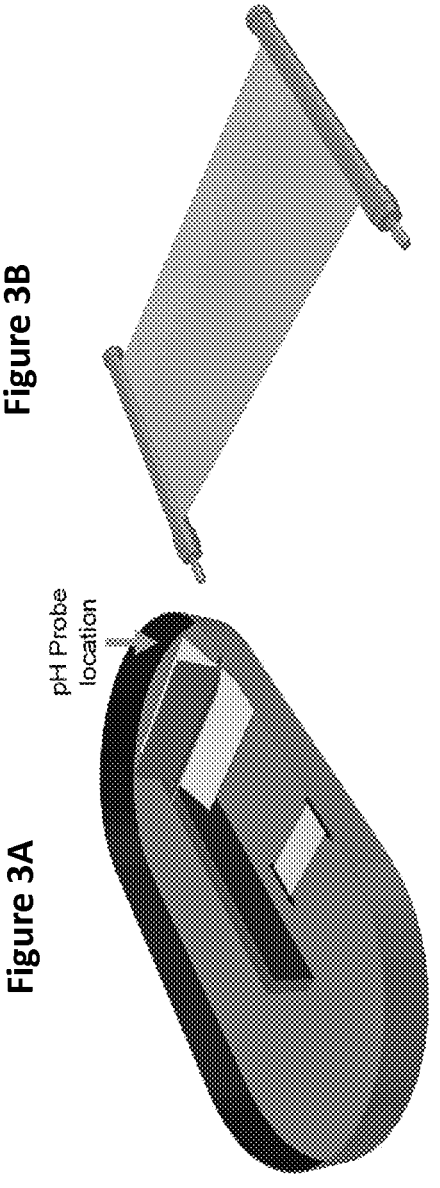
FIGS. 3A-3B are digital images of exemplary setups of MC sheets in outdoor raceways in accordance with embodiments described herein.

MC utilizes the direct transfer of $CO_2$ into the photoautotrophic culture. This is done by placing a bundle or sheet of fibers directly into the culture and using pH readings to control the $CO_2$ delivery rate through the MC fibers. MC can be used in multiple reactors with various gas sources/$CO_2$ concentrations. For bubble column and flat-panel reactor designs, MC bundles are placed in the reactor (FIG. 2) and an aerating driving force or mechanical mixing device is used to move the culture in a homogenous method to deliver the $CO_2$ to the entire culture. For raceways, a flat sheet design (FIGS. 3A-3B) is used to minimize the effect on the culture flow, by allowing the culture to flow across the fibers. pH-based control of algae cultures has been extensively demonstrated, as growing cultures consume $CO_2$ and bicarbonate, which increases the culture pH by producing large amounts of hydroxides. Therefore, the use of increasing pH as an indicator of carbon limitation and to trigger $CO_2$ delivery is the most efficient method of managing $CO_2$ delivery.

Operation of MC using 100% $CO_2$ or $CO_2$ mixed with other gases, such as in flue gas (5-15% $CO_2$, 5-10% $O_2$, 80-85% $N_2$), fermentation gas (80-100% $CO_2$, 0-20% $N_2$), biogas from anaerobic digesters (30-40% $CO_2$, 60-70% $CH_4$, 20-200 ppm $H_2S$) or landfills (50% $CO_2$ with balance of $CH_4$, $H_2S$, $H_2O$), biomass combustion gas (15-35% $CO_2$, with balance of $N_2$, $SO_2$, $NO$, $H_2O$) and gas from cement kilns (50% $CO_2$ with balance of $N_2$, $O_2$, $NO$), requires specific techniques to ensure high $CO_2$-transfer efficiency, while maintaining high fluxes through the hollow fiber membrane (HFM) surface; this minimizes the required surface area for $CO_2$ delivery to cultures. A principle of the disclosure being described below is the application and operational methods required to efficiently deliver $CO_2$ using HFM. This is done by manipulating the approach to the distal end of the fibers, which are connected to a valve. In embodiments, a solenoid valve on the inlet is used to maintain the pH of the culture. MC using high concentrations of $CO_2$ requires purging accumulated water vapor and inert gases from the fibers, typically once or twice per day, via a standard solenoid valve at the distal end of the fibers. The use of continuous bleed valves or intermittent solenoid bleed valves in mixed-$CO_2$ gases ensures high $CO_2$-transfer efficiency, while minimizing the buildup of inert gases and lowering of $CO_2$ flux rates. Inert gases are defined as gases in the feed gas that do not have a driving force into the medium due to low solubility or lack a concentration gradient due to no uptake or removal by the microalgae, for example, nitrogen gas.

When MC is used to feed algae $CO_2$ from gases that contain other gases, where one of the non-$CO_2$ gas is more valuable, MC can enrich the vented gas to have a higher purity of the high-value gas by selectively delivering $CO_2$ to the algal culture and removing it from the influent.

As disclosed herein, MC modules have similar build concepts, but can vary with application, reactor design, and scale. Exemplary MC modules contain a membrane unit operated with an inlet and distal end (not a U-shaped fiber design with both ends being inlets which prevents the ability to vent inert gases), valves on the inlet and outlet of the MC unit, and control software for operating the valves.

Exemplary embodiments of a MC sheet module, in addition to the valves and control software, includes a weighted frame to keep the fibers submerged below the surface level in the algae raceway. In one example, the membrane unit consists of composite hollow fiber membranes (Mitsubishi Rayon MHF 200TL) in a curtain/sheet design to allow for a flat surface area. In some embodiments, the fiber length is between 5 and 200 cm, with a minimum of 32 fibers and a maximum 100,000 fibers. In one particular embodiment, 1600 fibers at a length of 40 cm are used. In some embodiments, a range of 0.05 to 10 $m^2$-fiber SA/Raceway SA, such as ~0.1 $m^2/m^2$. The membranes use existing potting methods for curtain design to create an airtight manifold at each end of the fibers. In brief, the fibers are capped with a high viscosity adhesive to prevent fouling of the fibers. In some embodiments, 2-part epoxy adhesives are used. In some examples, 3 M polyurethane is used. For the sheet module, for example, a 2-part marine epoxy from epoxy/polyamide resin under the commercial name of Max Bond can be used. This adhesive is the same in both the high and low viscosity versions. It is contemplated that a variety of adhesives can be used, such as any adhesive which is waterproof and handles pressurization.

Next, the fiber bundles are inserted into a prefabricated mold, such as one that is about 15 to 100 cm long (including 15, 20, 25, 30, 40, 45, 50, 55, 60, 65, 70, 75, 80, 85, 90, 95 or 100 cm in length), about 1 to 2 cm wide (such as 1.1, 1.2, 1.3, 1.4, 1.5, 1.6, 1.7, 1.8, 1.9 or 2 cm in width), and about 0.75-2 cm deep (such as 0.75, 0.8, 0.9, 1.0, 1.1, 1.2, 1.3, 1.4, 1.5, 1.6, 1.7, 1.8, 1.9 or 2 cm in depth), and filled with a low viscosity adhesive, such as marine epoxy, to form a gas tight seal at both ends of the fiber sheet. Once set, the sealed fiber ends are removed from the mold and the formed ends are cut to remove a portion of the molded component, such as 0.25 cm of the molded component, to provide open (non-plugged) fibers. This molded end cap is then secured into a precut channel, such as in 1 inch PVC, and sealed with adhesive, such as the same adhesive, as the fiber form molding process first, thick, then thin set to create the air-tight manifold chamber. The ends of the PVC are connected to adapters, such as slip-to-thread adapters 1 inch to ½ inch national pipe thread (NPT), which are used to insert additional threaded adapters, such as a Push-to-Connect adapter, for the gas lines. The membrane unit is then affixed to a frame with desired dimensions dependent upon the length and width of the membrane curtain/sheet. In one example, the frame is a metal frame with dimensions of 45 cm long×20 cm wide. The purpose of the frame is to maintain the flat sheet shape of the flexible membrane unit and to ensure it remains submerged within the culture. In one example, a metal frame includes two 1-inch steel angle iron pieces to attach the membrane unit and two ¼ inch stainless steel rods to create a rectangular frame with the two pieces of angle iron. To prevent rusting, the frame is coated with a protective coating, such as waterproof paint. The module is connected to a gas source, such as with tubing, including ¼ inch polyurethane tubing at the inlet. In between the gas source and the module, a pressure regulator maintains the pressure of the membrane unit at the desired pressure, such as between 2 and 30 psig, including between 10 and 20 psig, such as about 2 psig, 3 psig, 4 psig, 5 psig, 6 psig, 7 psig, 8 psig, 9 psig, 10 psig, 11 psig, 12 psig, 13 psig, 14 psig, 15 psig, 16 psig, 17 psig 18 psig, 19 psig, 20 psig, 21 psig, 22 psig, 23 psig, 24 psig, 25 psig, 26 psig, 27 psig, 28 psig, 29 psig or 30 psig. Between the regulator and the MC unit, the gas line connects to a solenoid valve. In embodiments, the solenoid valve is typically in a closed position. On the outlet of the MC unit, the gas line tubing, such as ¼ inch polyurethane tubing, that connects to another solenoid valve. In another embodiment, the outlet of the MC unit has a pressure relief valve mixed with a needle valve to provide a continual flow outlet when the inlet valve is opened for gases with low $CO_2$ concentrations, such as flue gas and biogas.

In embodiments, MC units for indoor culture are designed to operate in cylindrical containers, flat panels, and bubble column reactors and can include 32 fibers (MR) at an approximate length of 17 cm. These units are connected to gas lines of appropriate size, such as ¼-inch gas lines, made of, for example, PVC, polyurethane, stainless steel, or tygon. The inlet gas line is connected to a gas cylinder with a regulator operating between 2 and 30 psig, which was then connected to a solenoid valve. The outlet gas line is connected to a solenoid valve and/or a bleed valve. In this operation, a solenoid valve is operated under a temporary purge protocol. This method utilizes a venting to atmospheric pressure to create a sweep gas that removes the accumulation of inert gases and/or water condensate from the lumen of the fiber. This is accomplished by using a solenoid valve on the distal end, which is opened when a secondary (elevated) pH setpoint is reached. This indicates that the flux of $CO_2$ through the fiber is lower than the operational demand of the culture, which when properly sized, is attributed only to water condensate or inert gas accumulation. To prevent excessive loss of $CO_2$, the purge time is based on the approximate time to replace the volume of gas within the MC unit. This method is suited to operations that require purging to occur at most 2 times per day for solenoid only operation. Solenoid/bleed combined valves can be operated at a higher frequency and for longer periods of time due to the reduced outflow of the bleed valve. For example, when the solenoid valve is supplied with power it opens in milliseconds, which creates an instant pressure drop to atmosphere. This creates an expansion of gas in the lines that will sweep out the inert gases/water vapor. The length of time open will depend upon the size of the system and the outlet flowrate. But ideally, the valve would be open long enough to remove the volume of gas contained in the gas lines next to the HFMs and HFMs.

The use of bleed valves in mixed $CO_2$ gases ensure high $CO_2$-transfer efficiency, while minimizing the effect of inert gases on $CO_2$ flux rates. In some examples, a bleed valve is a restricted valve at the distal end of the fiber designed to prevent the accumulation of inert gasses, while maintaining a pressure similar to fiber inlet. The bleed valve, compared to a standard purge solenoid, allows for a relatively constant flow of gas out the distal end of the fiber, when the solenoid valve at the inlet of the fibers is opened. The bleed valve is designed for use in <100% $CO_2$ feed gases and is used to restrict the flow to ensure <10% of the $CO_2$ exits the distal end of the fiber. In this case, the gases exiting the fiber are vented to the atmosphere and not retained.

In some examples, the disclosed methods and systems provide biologically-driven membrane gas separation. For instance, non-porous HFMs can be pressurized with gases that diffuse into an exterior liquid based on the concentration gradient from the membrane lumen to the exterior liquid. When the membrane contains a mixture of gases with similar mass transfer coefficients the concentration gradient dominates the mass transfer rates. Biological microorganisms consume a variety of gases when dissolved in liquid media as part of their normal or engineered metabolisms, including $CO_2$, $H_2S$, CO, $CH_4$, $NH_3$, $O_2$, $H_2$, which deplete the gas concentration within the liquid growth medium. As such, specific biological organisms or consortia are used to selectively remove specific gases from a mixed gas stream through HFMs. One application is for processing industrial waste gas streams containing gas mixtures including valuable gases or gases that are harmful to humans, the environment or industrial processes. For example, 1) $CO_2$ can reduce the efficiency of forming syngas or combusting biogas, 2) CO is known to poison synthetic catalysts and is toxic to humans and most biological organisms, 3) $CH_4$ and $NH_3$ are harmful greenhouse gases, 4) $O_2$ can deactivate oxygen sensitive catalysts and processes, 5) $NH_3$ and $H_2S$ are toxic to humans and the environment, and 6) $H_2$ present in low concentration can still be used as a biological energy source.

In some examples, the mixed-gas source being used has a secondary gas that is more valuable when purified to a higher concentration and $CO_2$ is removed. In these scenarios, it is beneficial to utilize the bleed valve approach, but instead of venting the exiting gases to the atmosphere, the gases are captured for further use. An example of this is the use of biogas as a feedstock for delivering $CO_2$ to the algal cultures. In this scenario, the biogas, which contains a high concentration of methane (approximately 65%) and $CO_2$ (approximately 35%), and low levels of $H_2S$ (20 to 200 ppm), is feed through the MC using pH control to open the primary delivery solenoid in front of the MC unit so that $CO_2$ is removed as the microalgae consume it, and a bleed valve at the end of the fiber allow the methane to exit at a significantly higher concentration. In addition, the process will be able to remove $H_2S$ from the biogas, which will further decrease downstream purification steps.

In another embodiment, co-cultures of a microalgae and a $H_2S$ oxidizing microorganisms, such as bacteria, are used to selectively remove $CO_2$ and $H_2S$ from the biogas. In some examples, microalgae are co-cultured with an $H_2S$ oxidizing microorganism to remove $CO_2$ and $H_2S$ from biogas to enrich the $CH_4$ content exiting the fiber. In some embodiments, the disclosed methods and systems utilize syngas as a feedstock for delivering $CO_2$ (typically about 15%) to the cultures, such as algal cultures, to enrich the remaining gases—$H_2$, CO, and $CH_4$. In some embodiments, microalgae are co-cultured with an $H_2S$ oxidizing microorganism to remove $CO_2$ and $H_2S$ from syngas from the gas mixture exiting the fiber. Exemplary $H_2S$ oxidizing microorganisms include, but are not limited to, Beggiatoaceae, purple sulfur bacteria, green sulfur bacteria, *Acidithiobacillus*, *Aquaspirillum*, *Aquifex*, *Bacillus*, *Methylobacterium*, *Paracoccus*, *Pseudomonas*, *Starkeya*, *Thermithiobacillus*, or *Xanthobacter*.

In some embodiments, the microalgae are replaced with a CO oxidizing microorganism to remove it from a mixed gas containing CO. Exemplary CO-oxidizing microorganisms include, but are not limited to Oligotropha, Stappia, or Mycobacterium. In some embodiments, the mixed gas is flue gas from a natural gas, oil, wood, coal or other any other carbon-based fuel combusted in a power plant.

In some embodiments, the microalgae are replaced with a $CH_4$-oxidizing microorganism to remove it from a mixed gas, such as biogas, containing $CH_4$. Exemplary $CH_4$-oxidizing microorganism include, but are not limited to, Methylococcaceae, Methylocystaceae, Gammaproteobacteria, or Alphaproteobacteria.

In some embodiments, $NH_3$ is removed from a mixed gas for cultivating nitrifying bacteria, such as *Nitrosomonas* or *Nitrosococcus*. For example, the mixed gas is from livestock manure off-gassing and/or from fertilizer production.

In some embodiments, $O_2$ is removed from a mixed gas and consumed by microorganism performing respiration, such as *E. coli, Shewanella oneidensis*, and *Marinobacter aquaeolei*.

In some embodiments, $H_2$ is removed from a mixed gas and consumed by $H_2$ oxidizing bacteria. Exemplary $H_2$ oxidizing bacteria include, but are not limited to, *Hydrogenobacter thermophilus, Cupriavidus necator, Hydrogenovibrio marinus*, and/or *Helicobacter pylori*.

The disclosed methods and systems have several advantages. Existing technology used for the delivery of gaseous $CO_2$ to cultures requires the use of bubbles to deliver $CO_2$ into the culture solution. Several limitations are associated with bubbling into cultures. 1) Bubbling requires sufficient contact time to transfer the $CO_2$ into the liquid phase, but gas bubbles are buoyant and have a short contact time with the culture. To overcome this concern, existing technology utilizes either sumps or carbonation columns to extend the water column height to increase the bubble contact time. This requires additional infrastructure and energy costs. MC does not need an extended water column to deliver $CO_2$ to the solution, which allows for placement at any location within the culture. 2) Capturing exiting gas is impossible in traditional technologies. The only other technology that can capture the exiting gas is a carbonation column design, which has been demonstrated to have potential using algal cultures to upgrade biogas to biomethane. However, existing technology has significant challenges with the transfer of $O_2$ into the biogas, which diminishes its quality. MC significantly reduces the transfer of $O_2$ into the biogas as the transfer rate of $CO_2$ into the liquid cultures is significantly higher than the back diffusion of $O_2$ into the fiber lumen. 3) Using microporous membranes have two main problems. During the day, when $CO_2$ is being delivered, a lumen pressure very close to the hydrostatic pressure is needed to prevent bubble formation. This is not realistic to do, because the hydrostatic pressure is so low in normal systems. At night, when $CO_2$ is not being delivered, no lumen pressure is desired, which results in water filling the fibers, causing serious problems with plugging. Non-porous HFM address these problems and are thus better than microporous HFM, as they do not require a constantly controlled pressure to prevent the algae culture from seeping into the fibers at night and from forming bubbles when delivering $CO_2$. This reduces the run time and energy associated with the HFM system. Non-porous HFM can operate at variable pressures to regulate the flux of $CO_2$, while microporous HFM must have a narrow operating pressure to ensure that active bubble formation does not occur and that enough pressure is available to a positive pressure along the length of the fiber to ensure seepage does not occur.

Thus, the disclosed methods are superior to existing technologies for at least the following properties: 1) use of bubbleless $CO_2$ transfer, which increases, such as by 10% or more, the $CO_2$ transfer efficiency into the culture medium; 2) use of feed gases with a wide range of $CO_2$ concentration, while maintaining the desired on-demand $CO_2$ delivery, such as the rate varies over time and the HFMs allow on-demand control of the delivery rate, further having a transfer efficiency greater than 90%; 3) ability to concentrate valuable gases that are mixed with $CO_2$, such as methane in biogas; and 4) low gas-pressure separation of $CO_2$ and methane.

Existing technology for separating biogas via membrane upgrading utilizes either high pressure with non-porous gas-gas interaction or microporous with a gas-liquid interface. For non-porous, solubility of the gases in the membrane and high partial pressures are used to separate $CO_2$ from methane. However, the methodology requires significant compression compared to the inclusive technology in this form. The use of microporous HFM in a gas-liquid interface to increase the driving force for $CO_2$ through the membrane, by creating a carbon sink. The challenge with existing technology is that the methods use microporous membranes and also needs a method to regenerate the amine solution.

The disclosure is further illustrated by the following non-limiting Example.

EXAMPLES

Example 1

Direct Membrane Carbonation of a Fresh Water Green Alga, *Scenedesmus acutus*, and a Salt Water Coccolithophore, *Emiliania huxleyi*

*Scenedesmus acutus* (0401) was grown in standard BG-11 medium (per liter) containing 17.6 mM $NaNO_3$, 0.23 mM $K_2HPO_4$, 0.30 mM $MgSO_4$, 0.24 mM $CaCl_2$, 0.01 mM citric acid, 0.021 mM ferric ammonium citrate, 0.0027 mM $Na_2EDTA$, 0.19 mM $Na_2CO_3$, and trace metals was used for biomass cultivation. *Emiliania huxleyi* (Ehux) was grown in Defined Instant Ocean Erdschrieber's Media (DIO-ESM) having 2.8 mM $NaNO_3$ and 7.4 μM $KH_2PO_4$.

Figure 4:
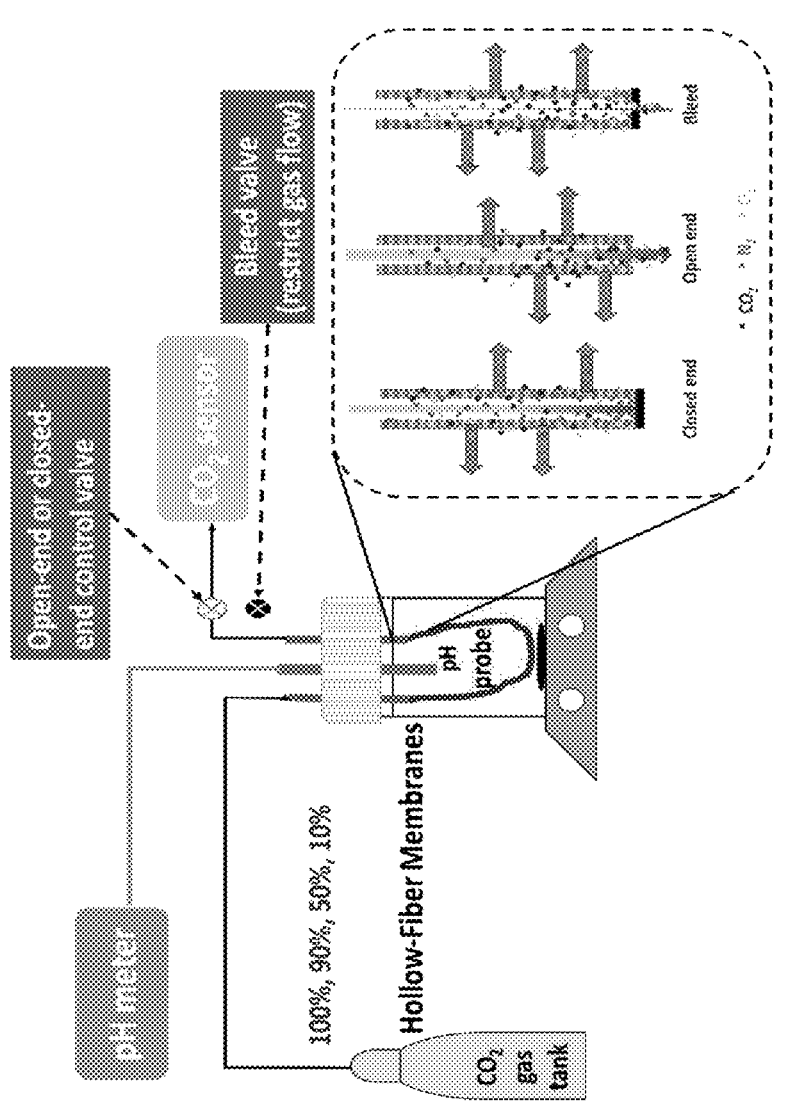
FIG. 4 is a schematic diagram for testing $CO_2$-delivery strategies by pH-controlled delivery and venting with gas supplies having 10, 50, 90 or 100% $CO_2$ in accordance with embodiments disclosed herein.

Cultures utilized MC to deliver $CO_2$ at concentrations of 100%, 90% 50%, or 10% $CO_2$, mixed with air. pH control, $CO_2$-capture efficiency, biomass growth rates, and biomass composition were evaluated for different MC operating scenarios, as well as sparging with 100% $CO_2$ as illustrated in FIG. 4. Cultures were operated with a 6-d solids retention time. For MC, bundles of hollow fiber membranes (HFMs) were suspended in 700-mL wide-mouth glass bottles, for Ehux, and 2-L wide-mouth bottles for 0401 illuminated by 100 μE/m$^2$·s fluorescent lamps. The stirring plates (Thermo Fisher Scientific, USA) were consistently operated at 450 rpm. The venting setups were evaluated with 100%, 90%, 50% and 10% $CO_2$ gas and only 10% $CO_2$ case with an additional bleed-valve test. The sparging system with 100% $CO_2$ gas was evaluated in parallel with membrane carbonation studies and the sparging gas flow was maintained as 10 ccm by the flow controller (MC Series, ALICAT Scientific, USA). The pH of culture media was maintained by pH-Stat system (Neptune System, CA, U.S.). The fibers had a solenoid valve (MA955, Milwaukee Instruments, USA) on the inlet side, and it was opened or closed in response to the culture's pH. When the pH was higher than the set point (pH=8.0 for 0401 and 8.2 for Ehux), the valve was opened so that $CO_2$ was delivered. When the pH dropped below the set point (pH=7.9 for 0401 and 8.19 for Ehux), the inlet valve was closed. venting valve was installed on the distal end of the fibers. The venting valve was opened and closed independently based on a secondary, higher pH set point (pH=8.05 for 0401 and 8.25 for Ehux), which was slightly higher than the pH set point for the inlet valve. The vent valve was closed, when the set pH was below 8.03 and 8.24, respectively. The purpose of opening the vent valve is to flush the membrane lumen of inert gas before it significantly slowed the $CO_2$ delivery rate. To minimize the loss of $CO_2$, the outlet was installed with a pressure gauge (ALICAT Scientific, USA) to create a bleed valve scenario to restrict the outlet flow to 2.2 cubic centimeters per minutes (ccm). The bleed valve remained open and did not depend on pH in the media. The vented or exhausted $CO_2$ gas was monitored by $CO_2$ sensors (COZIR Wide Range 100% $CO_2$ and K33 BLG 30% $CO_2$, CO2Meter.com, FL, USA) that were installed at the outlet of fiber module. The dissolved oxygen (dissolved oxygen probe, Orion 083005MD, USA) was checked periodically in the photobioreactors to track the fluctuation of oxygen levels during the biomass growth.

Figure 5A:
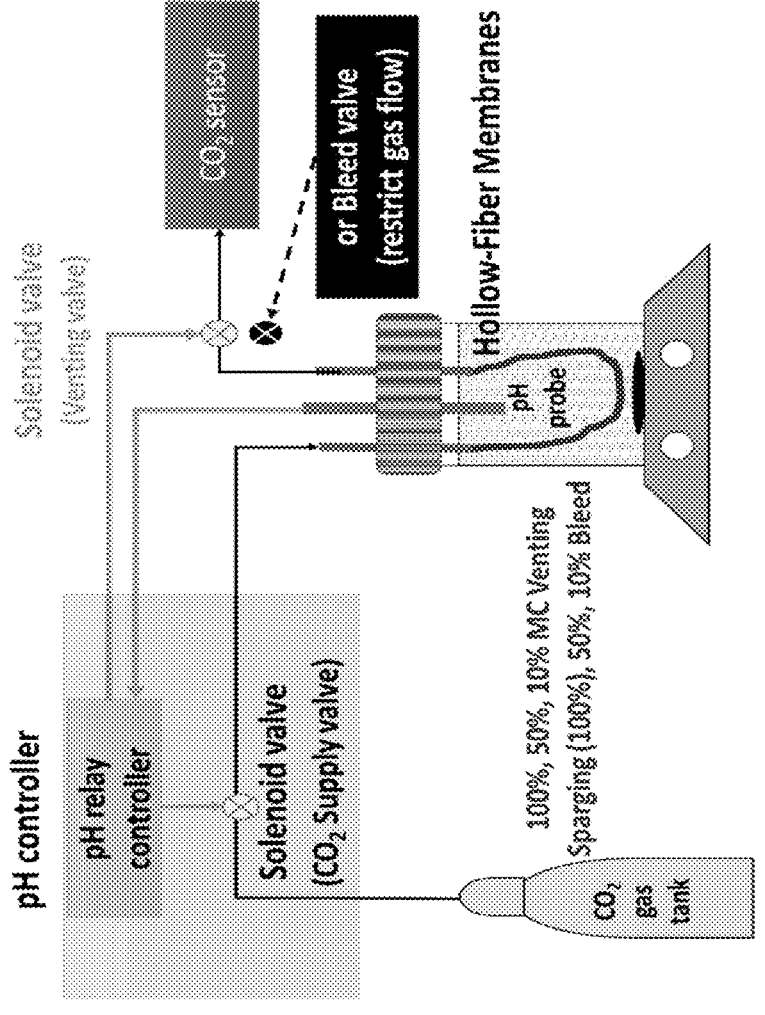
FIG. 5A is a schematic diagram for for testing $CO_2$-delivery strategies by pH-controlled delivery and venting with gas supplies having 10, 50, or 100% $CO_2$ (in which sparging did not use the hollow fiber membranes (HFMs)) in accordance with embodiments disclosed herein.

FIGS. 4 and 5A provide a schematic diagram for testing $CO_2$-delivery strategies by pH-controlled delivery and venting with gas supplies having 10, 50, or 100% $CO_2$. Sparging did not use the HFMs.

Fiber Bundle Preparation and $CO_2$ Flux Evaluation

The composite hollow fiber membrane (Model MHF 200TL, Mitsubishi-Rayon Co., Ltd., Japan) was glued using the liquid resin (Max Bond, Polymer Composites Inc, USA) and each fiber module contained 32 fibers in total and about 17.5 cm in length. Each fiber module was checked using 100% $CO_2$ at 10 psig to ensure no gas leakage from the epoxied part and consistent gas flow with a gas flow meter (MC Series, ALICAT Scientific, USA) prior to running flux tests and biomass cultivation.

$CO_2$ Flux Estimation

The $CO_2$ fluxes (g-$CO_2$/m$^2$-hr) were estimated according to Eq (1), where SA is the membrane surface, and the flux is computed as the $CO_2$ mass delivered within the time window Δt. The total $CO_2$ ($m_{CO2}$) was computed from $C_T$ (mM) and reactor volume (V). Inorganic carbon, $C_T$, could be computed from the known total alkalinity, $[Alk]_0$, and ionization factors $\alpha_1$ and $\alpha_2$ for $HCO_3^-$ and $CO_3^{2-}$, respectively.

$$J_{CO_2} = \frac{(m_{CO_2})_{i+\Delta t} - (m_{CO_2})_i}{SA \times \Delta t} \qquad \text{Eq (1)}$$

$$m_{CO_2} = MW_{CO_2} \times C_T \times V \qquad \text{Eq (2)}$$

$$C_T = \frac{[Alk]_0 - \frac{K_W}{[H^+]} + [H^+]}{\alpha_1 + 2\alpha_2} \qquad \text{Eq (3)}$$

$$\alpha_1 = \alpha_{HCO_3^-} = \frac{[H^+]K_1}{[H^+]^2 + [H^+]K_1 + K_1K_2} = \frac{[HCO_3^-]}{C_T} \qquad \text{Eq (4)}$$

$$\alpha_2 = \alpha_{CO_3^{2-}} = \frac{[H^+]K_1K_2}{[H^+]^2 + [H^+]K_1 + K_1K_2} = \frac{[CO_3^{2-}]}{C_T} \qquad \text{Eq (5)}$$

The analytical definition of alkalinity, $[Alk]_0$, is described as below. The total alkalinity was given at 10 mM for all experiments.

$$[Alk]_0 = [HCO_3^-] + 2[CO_3^{2-}] + [OH^-][H^+] \qquad \text{Eq (6)}$$

Carbon-Utilization Efficiency and Carbon-Transfer Efficiency

The carbon utilization efficiency (CUE) and carbon transfer efficiency (CTE) were estimated based upon the Eq (7) and Eq (8), respectively below. The unit was carbon basis (g).

$$CUE(\%) = \frac{Biomass{-}C}{Biomass{-}C + net\ DIC + C{-}CO_2\ gas\ loss} \times 100\% \qquad \text{Eq (7)}$$

$$CTE(\%) = \frac{Biomass{-}C + net\ DIC}{Biomass{-}C + net\ DIC + C{-}CO_2\ gas\ loss} \times 100\% \qquad \text{Eq (8)}$$

where biomass-C represented $CO_2$ utilization converted to biomass, 1 g biomass production was required 1.82 g $CO_2$ supply. Net dissolved inorganic carbon (DIC) value was difference of DIC in the culture media between before and after feeding fresh media. DIC was quantified using TOC-V (Shimadzu, Japan). The sample preparation was documented. $CO_2$ gas loss was referral to the venting or bleed events. The off-gas $CO_2$ quantification involved with venting frequency, duration of venting, vented $CO_2$ concentration and gas flow of venting. For the sparging setup, it followed the same patterns for the $CO_2$ loss estimation. Based upon the previous studies (Kim et al., *Bioresource Technology* 204 (2016): 32-37), nearly 100% CTE could be achievable by 100% $CO_2$ gas. Here, no venting event was identified in 100% $CO_2$ operation. It was validated to claim that ~100% CTE could be achieved in a case of 100% $CO_2$ supply (if not including the net DIC value). The CTE results were obtained at semi continuous operation with 3-phosphate amendment conditions. Biomass dried weights, such as total suspended solids were determined using glass microfiber filter (GF/C, Whatman, USA) and were weighted after 90° C. incubation overnight and 2-hour cooling at room temperature in the desiccator.

Figures 5B, 5C:
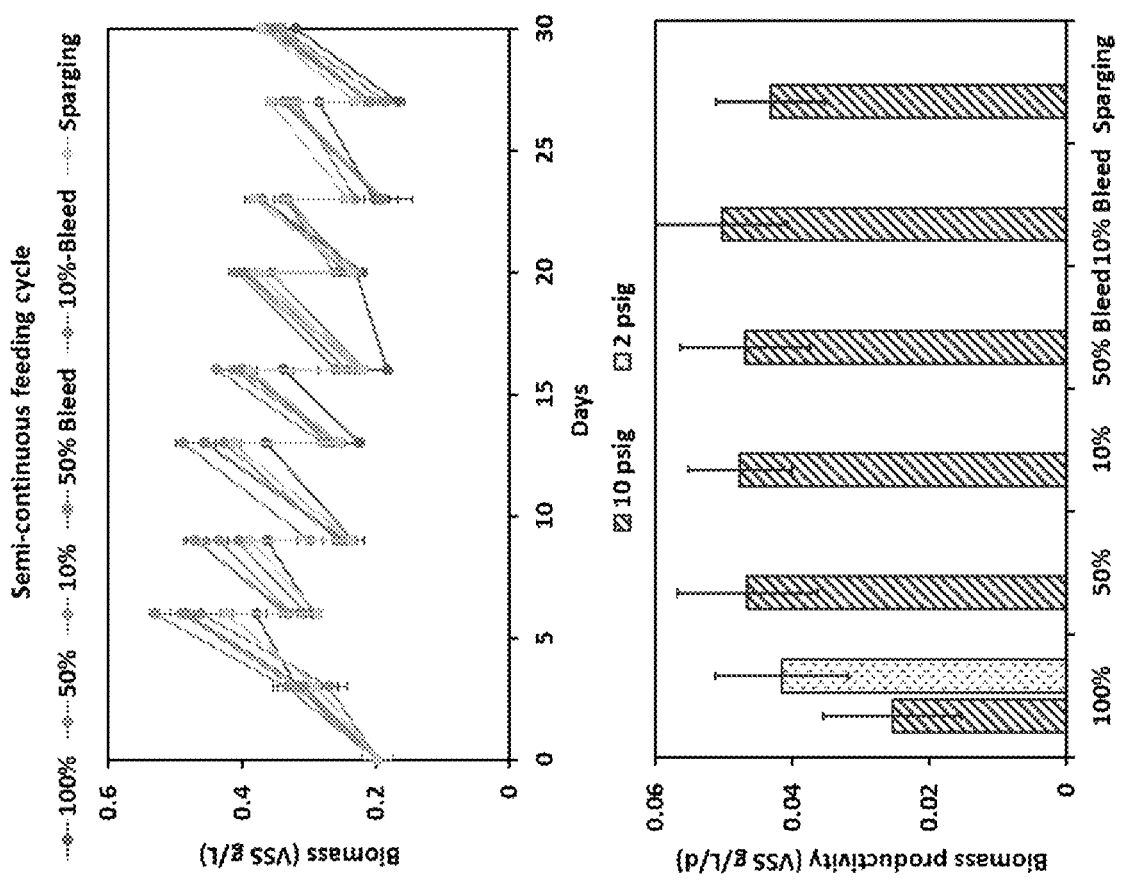
FIGS. 5B-5C illustrate biomass density and productivity for experimentation with *Emiliania huxleyi* for different $CO_2$ percentages in the feed gas.

FIGS. 5B and 5C show that biomass growth and productivity for Ehux were consistent for all operating conditions during semi-continuous cultivation with 10 psig, except for supplying 100% $CO_2$. The lower productivity could have been caused by a larger pH variation during delivery of 100% $CO_2$ at 10 psig, since *E. huxleyi* is sensitive to pH changes. When one reduced the pressure to 2 psig with 100% $CO_2$, the biomass productivity became similar to the other conditions.

Figure 6:
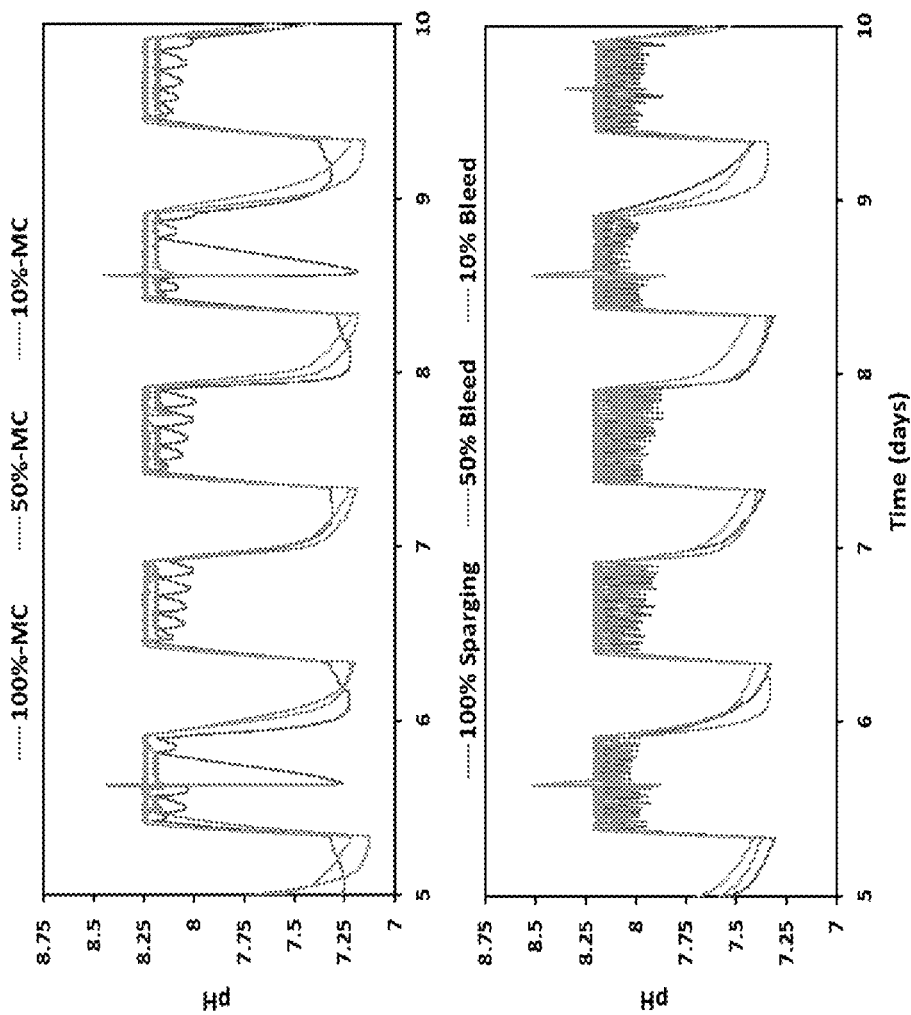
FIG. 6 illustrates pH variation for the several forms of $CO_2$ delivery when cultivation was operated in diurnal conditions.

Table 1 shows the valve-operation patterns during the semi-continuous feeding cycles, and FIG. 6 illustrates the pH patterns in those cycles. A strong trend was that delivering more-dilute $CO_2$ caused the supply valve to open more frequently (Table 1), but the pH variation was less (FIG. 6). For example, bleed-valve operation with 10% $CO_2$ had 69-99 supply-valve openings per day and a low pH of about 8.16, while 50% $CO_2$ had 18-24 openings per day and a low pH of about 7.9. Another trend was that the inlet valve was on less often for 10%-bleed than for 10% $CO_2$ open-end, since the bleed valve could drive more $CO_2$ into the culture media, which resulted in the pH dropping below the setpoint of pH 8.19 more often. Therefore, the supply valve would shut off more often with 10%-bleed.

TABLE 1

Frequency of automated valve operation based upon gas delivery strategies during the semi-continuous feeding cycles.

| | CO₂ Supply Valve | | CO₂ Venting Valve | |
|---|---|---|---|---|
| Scenarios | # of valve On-Off cycle (per day) | Duration between On and Off (sec) | # of valve On-Off cycle (per day) | Duration between On-Off (sec) |
| 100% | 6 | 16 ± 5 | 0 | Only occurred when feeding media |
| 50% | 34 | 27 ± 9 | 1-2 | 29 ± 18 |
| 10% | 1 | ~12.25 hrs | ~130 | 25 ± 6 |
| 50% Bleed | 18-24 | 13 ± 9 | N.A. | Bleed |
| 10% Bleed | 69-99 | 119 ± 18 | N.A. | Bleed |
| Sparging | 14-21 | 17 ± 3 | N.A. | N.A. |

Notes:
N.A. means that vent-valve opening was not applicable.
For the bleed value, it was always open with a small flow rate (up to 2.1 cubic centimeter per minute).
Sparging had no membranes and no venting valve.

Figures 7A, 7B, 7C:
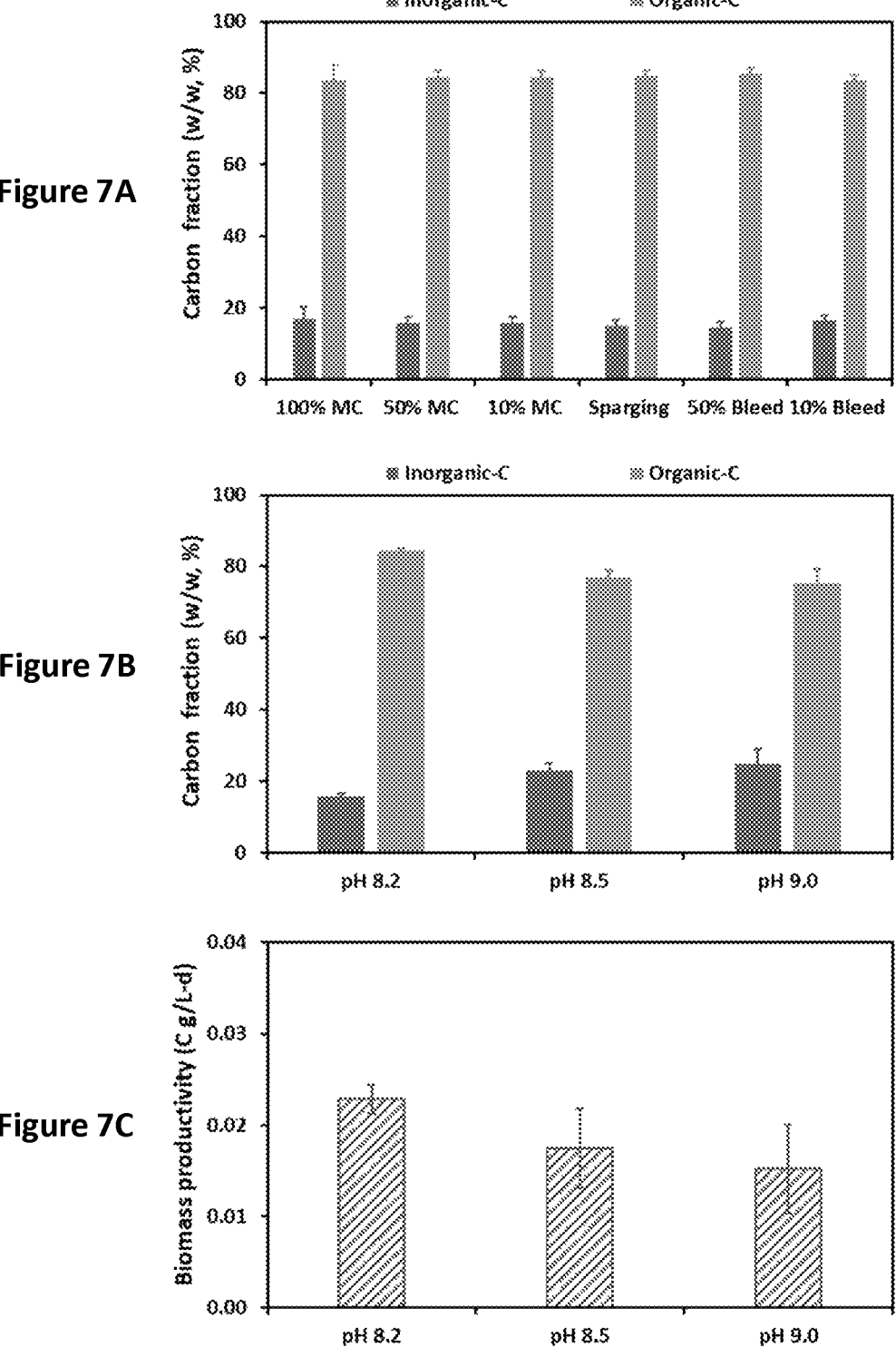
FIGS. 7A-7C illustrate inorganic and organic fractions of carbon production by *Emiliania huxleyi* at (7A) different operations with pH 8.2 and (7B) different pH set points with 50% $CO_2$ MC. The percentages are based on mg C/L (inorganic-C %=inorganic-C/total C; organic-C %=organic-C/total C). (7C) Total biomass productivity (as C) for the different pHs.

FIGS. 7A-7C show that the inorganic-(IC) and organic-carbon (OC) fractions of *Emiliania huxleyi* (Ehux) had consistent ratios for all $CO_2$ delivery strategies when the set-point pH was 8.2. However, the ratio shifted when the pH set point was increased to 8.5 and 9.0: The inorganic fractions was 56% for pH≥8.5, up from 43% at pH 8.2. On the one hand, the productivity of organic biomass declined with higher pH: 0.023±0.002 g (pH 8.2), 0.017±0.004 (pH 8.5) and 0.015±0.005 (pH 9.0) g/L-d. One the other hand, increasing pH led to a higher ratio of inorganic C to organic C. This means that one can raise the pH to promote the formation of inorganic C in *Emiliania huxleyi*, although the total productivity in g C/L-day slightly declined (FIG. 7C).

Figures 8A, 8B:
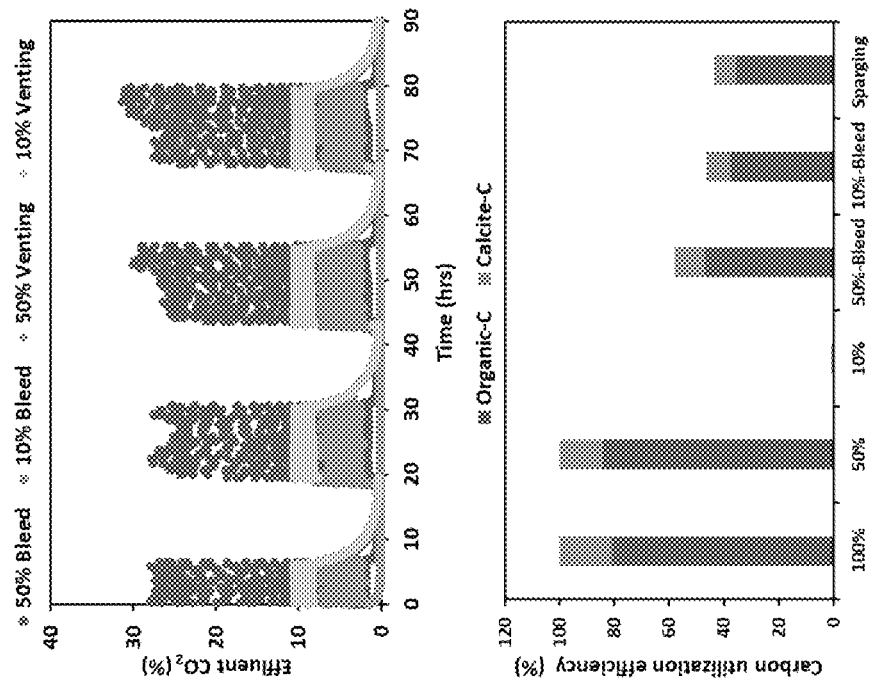
FIG. 8A illustrates $CO_2$ content for the gas vented through distal end of the membrane fibers.
FIG. 8B illustrates carbon utilization efficiency estimated on the basis of one-day carbon utilization to form biomass, 1.82 g $CO_2$/g organic biomass, and measured one-day $CO_2$ input.

FIG. 8A shows the $CO_2$ loss attributed to off-gassing during the venting and bleeding operations. For bleed-valve operation, the smallest loss was with 10% $CO_2$, since most of the vented gas was inert. However, the smallest loss overall was with 50% $CO_2$ using a venting valve, because the venting valve opened only 1 or 2 times per day. These results point out that the operating strategy depends on the $CO_2$ content of the supply gas. With 10% $CO_2$, the best strategy was a bleed valve, but the best strategy for 50% $CO_2$ was an automated venting valve. FIG. 8B shows that a good

US 12,649,898 B2

15

Figure 8C:
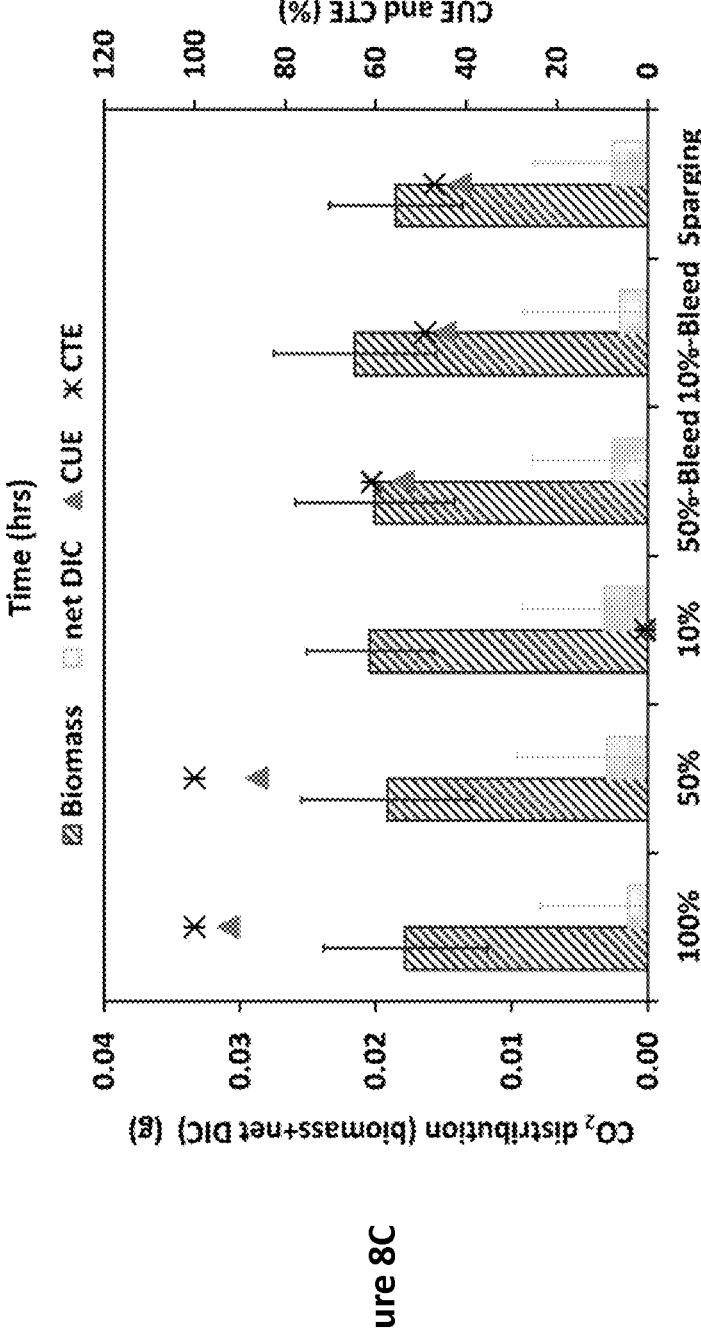
FIG. 8C illustrates carbon distribution estimated on the basis of carbon utilization to form biomass, 1.82 g $CO_2$/g organic biomass, and measured $CO_2$ input.

16 operating strategy could lead to nearly 100% efficiency of converting $CO_2$ into organic C plus inorganic C. Feeding 100% $CO_2$ or 50% $CO_2$ with a venting value yielded nearly 100% C capture, with about 55% organic C (at pH 8.2). The fact that *Emiliania huxleyi* converted $CO_2$ to the biomass and calcite was important for attaining the high efficiencies seen in FIGS. 8B and 8C. Lower efficiencies (approximately 20% $CO_2$ capture efficiency) have been obtained with *Scenedesmus*, which does not produce calcite. In term of improving carbon capture by MC, using *E. huxleyi* is advantageous.

Figure 9:
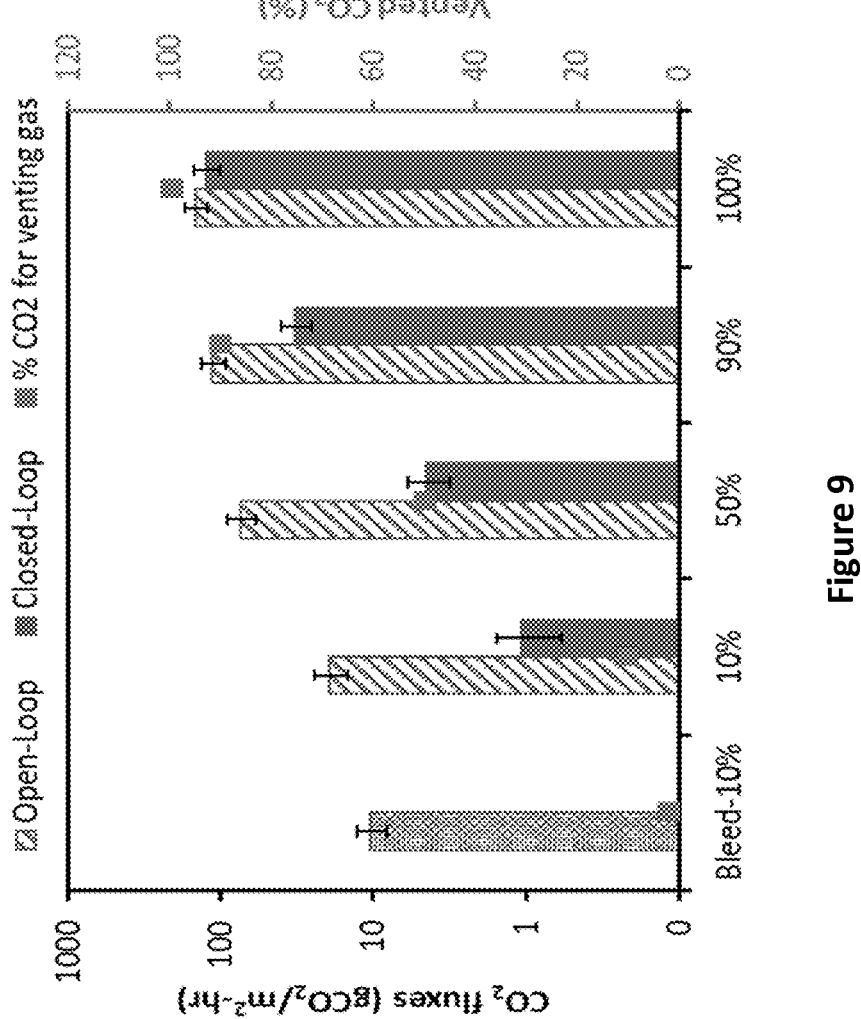
FIG. 9 is a bar graph showing the fluxes when 10%, 50%, 90%, and 100% $CO_2$ was delivered at 10 psig. Given gas pressure supply at 10 psig, $CO_2$ flux (bars) and concentration of $CO_2$ in exhaust gas when the vent valve is open. Bleed- 10% refers to the operational conditions of maintaining a steady exhaust rate of 2.2 sccm when the main $CO_2$ valve is open.

FIG. 9 shows the fluxes when 10%, 50%, 90%, and 100% $CO_2$ at 10 psig was delivered. To reduce the off-gassing occurring at 10% $CO_2$, a bleed valve was included, which restricted the exiting flow to 2.2 SCCM; without the bleed valve, the exit flow rate was 1665-1780 SCCM. Open-end operation was able to maintain slightly different $CO_2$ fluxes of 84±20, 150±32 and 170±31 g $CO_2/m^2$-hr, when using 50%, 90% and 100% $CO_2$, respectively, and the drop off in flux was moderated as 22±6 and 12±3 g $CO_2/m^2$-hr, for fully open and bleed-valve settings at 10% $CO_2$. For the full open-end operation at the same gas pressure supply, $CO_2$ fluxes was proportional to $CO_2$ percentage. However, when operated in closed-end mode, $CO_2$ fluxes dropped dramatically from 140±28 to 1.9±0.8 g $CO_2/m^2$-hr for 100% to 10% $CO_2$, respectively, corresponding to 18% to 90% declined ratio (closed-end vs open-end flux) from 100% to 10% $CO_2$ because of accumulating inert gases. Thus, severe declines in $CO_2$ flux associated with closed-end operation were mitigated using an open-end strategy. However, operation with an open-end led to $CO_2$ losses at the distal end of the fibers for all tested $CO_2$ gas. Basically, the exhausted $CO_2$ concentrations were similar to the applied $CO_2$ concentrations. Using a bleed valve on the distal end reduced $CO_2$ concentration exiting the fibers from 10% in a fully opened state to 2% $CO_2$ with the bleed valve (or 5-fold higher efficiency). A venting valve was also implemented to relieve accumulating inert gases while minimizing $CO_2$ loss out of the fiber ends.

Figure 10:
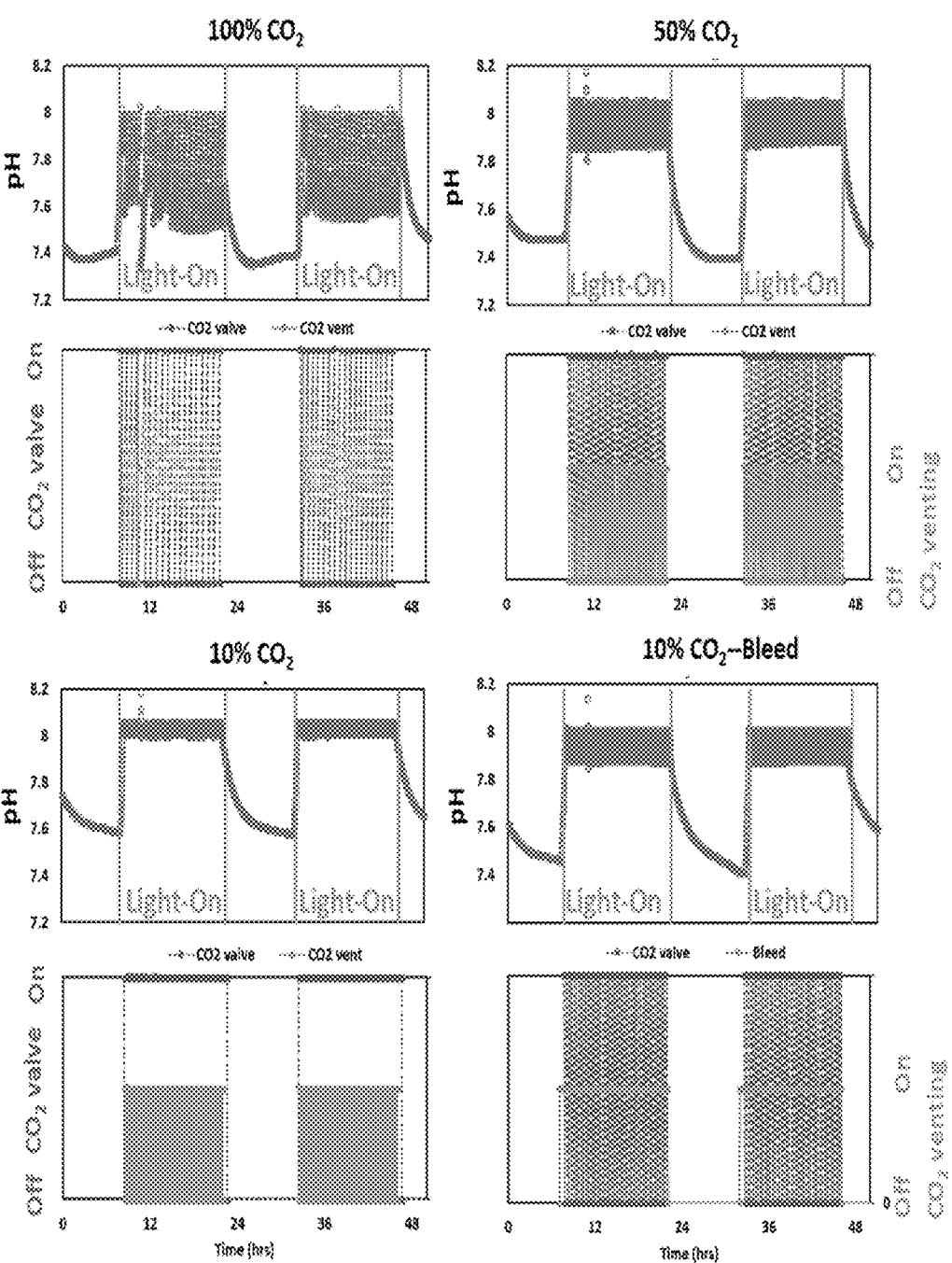
FIG. 10 shows the pH in the medium and the status of the inlet and vent valves during two days of continuous cultivation for various input-$CO_2$ concentrations.

FIG. 10 shows the pH in the medium and the status of the inlet and vent valves during two days of continuous cultivation for various input-$CO_2$ concentrations. $CO_2$ fluxes obtained from various $CO_2$ concentration and the operations (open- vs closed end) can be substantially different in two magnitudes, thus the solenoid valves were implemented to deliver $CO_2$ and mitigate $CO_2$ loss at distal end. The graphs highlighted that the pH could be maintained within a narrow range for all input-$CO_2$ concentrations, and the variated pH units were 0.5, 0.3, 0.2, <0.05, <0.15 and <0.15 for 100%, 90%, 50%, 10%, 10%-bleed and 100% sparging, respectively. pH control was the most precise when delivering 10% $CO_2$. The degree of pH variation during $CO_2$ delivery was correlated with given $CO_2$ fluxes (or concentration), i.e., high fluxes led to high pH variation. Small pH variation could also be obtained by the indoor sparging system, since it was equipped with a flow controller (MC Series, ALICAT Scientific, USA) with only 10 ccm gas flow. With pH-stat setups, $CO_2$ delivery was on demand, and the venting events occurred when $CO_2$ could not be sufficiently supplied. No venting for 100% $CO_2$ to a high frequency of venting for 10% (orange spikes). In addition, 10% $CO_2$ with lowest flux could not drop the pH below 7.9 (set point), and thus the $CO_2$ supply valve was never shut "off" during the "light on" period.

Figure 11:
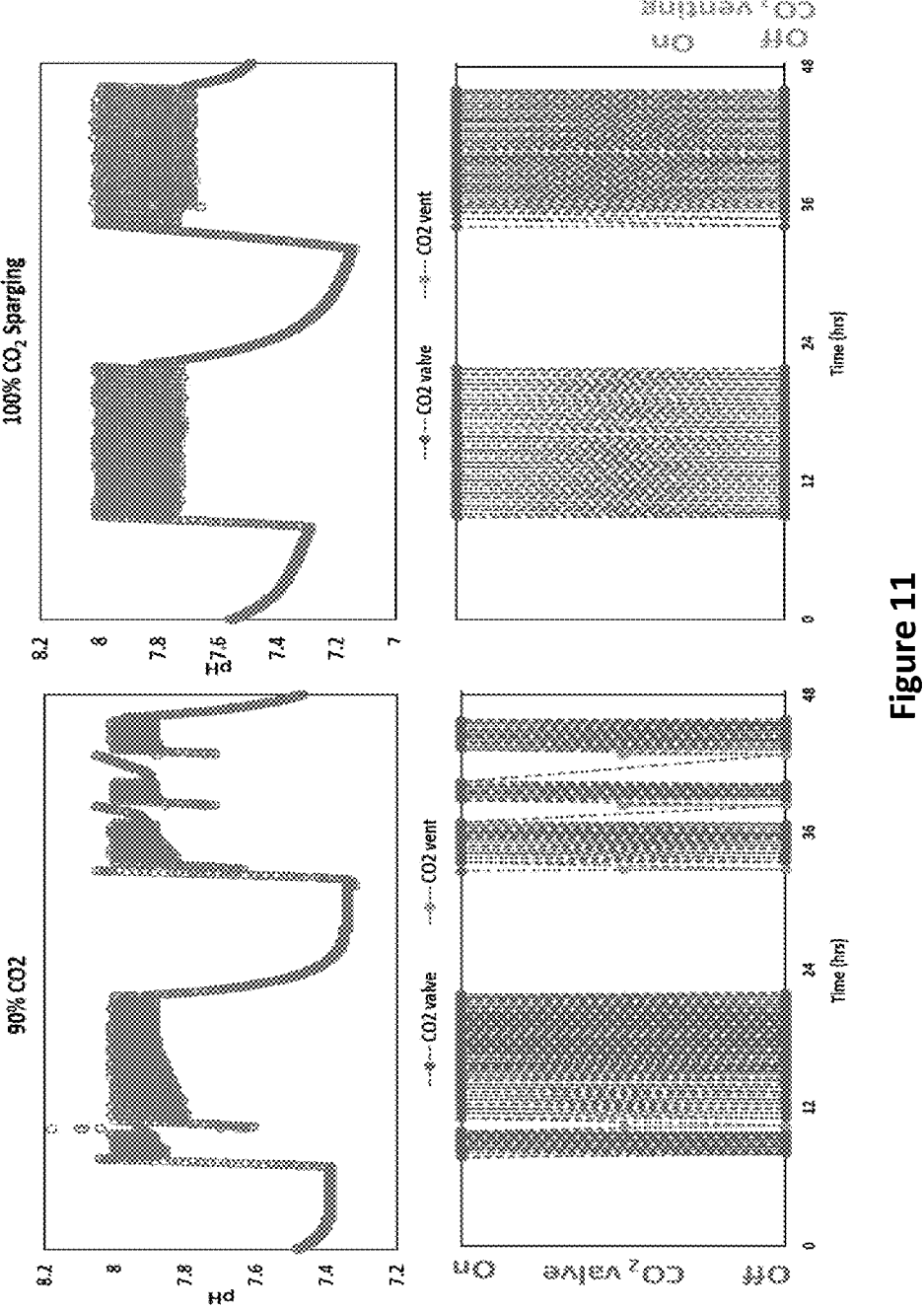
FIG. 11 illustrates pH-controlled operation with 90% $CO_2$ of inlet and venting allowed precise pH control vs 100% $CO_2$ sparging with restricted 10 ccm gas flow during the diurnal operation of cultures of *Scenedesmus acutus* in bench-scale PBRs.

FIG. 11 provides examples of how pH-controlled operation of inlet and venting allowed precise pH control during the diurnal operation of cultures of *Scenedesmus acutus* in bench-scale PBRs. The top panels show the variations of pH around the set-point of 8.0. The bottom panels show when the inlet valve was open (blue line) and when the venting value was open (orange line). 10%—Bleed means that the venting valve was restricted for a gas flow. The 90% $CO_2$ and 100% conventional sparging were documented in FIG. 11.

Figures 12A, 12B:
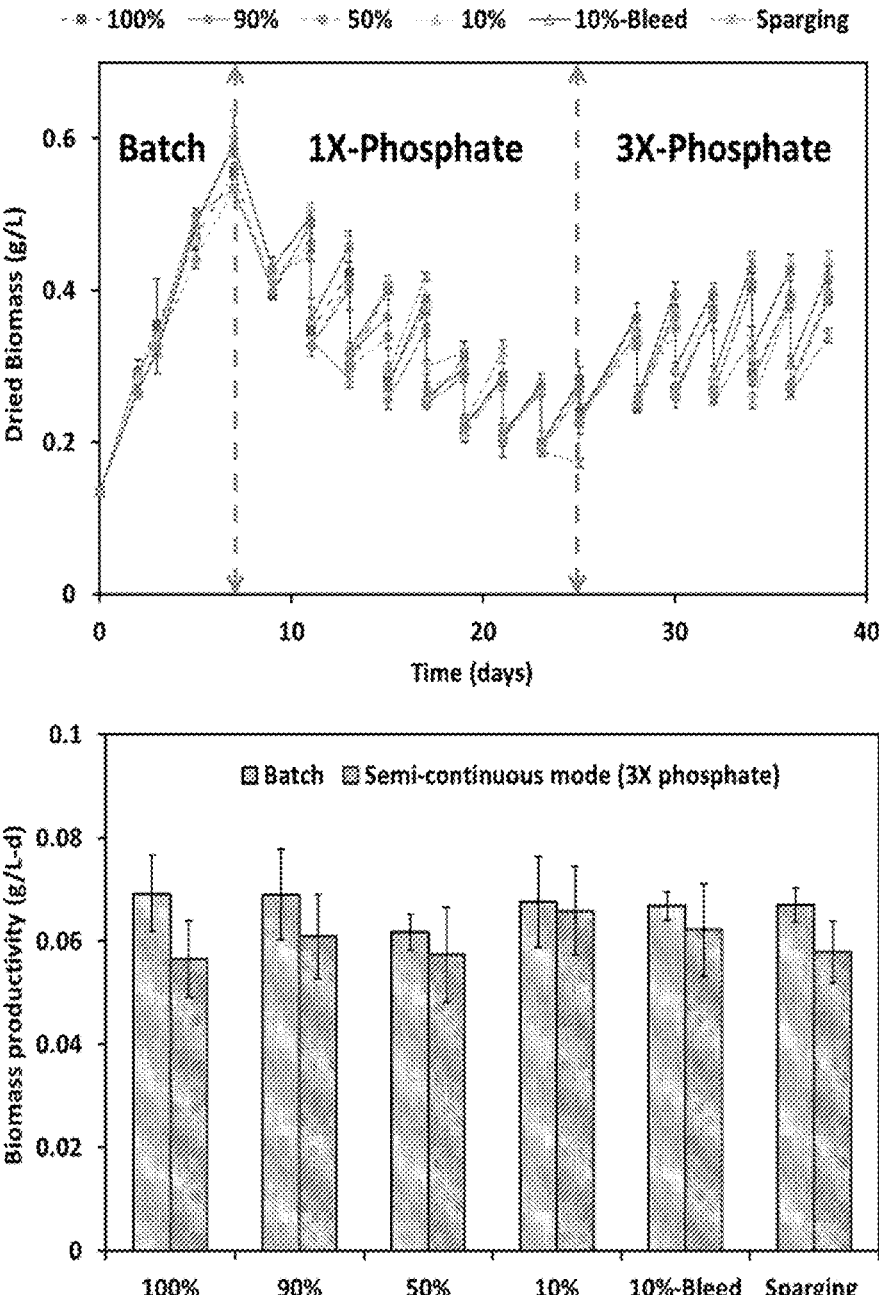
FIG. 12A. *Scenedesmus* biomass growth on all tested $CO_2$ concentrations was able to maintain a significantly similar productivity throughout the experiment.
FIG. 12B. Biomass productivity at different supplied $CO_2$ concentration.
Figure 13:
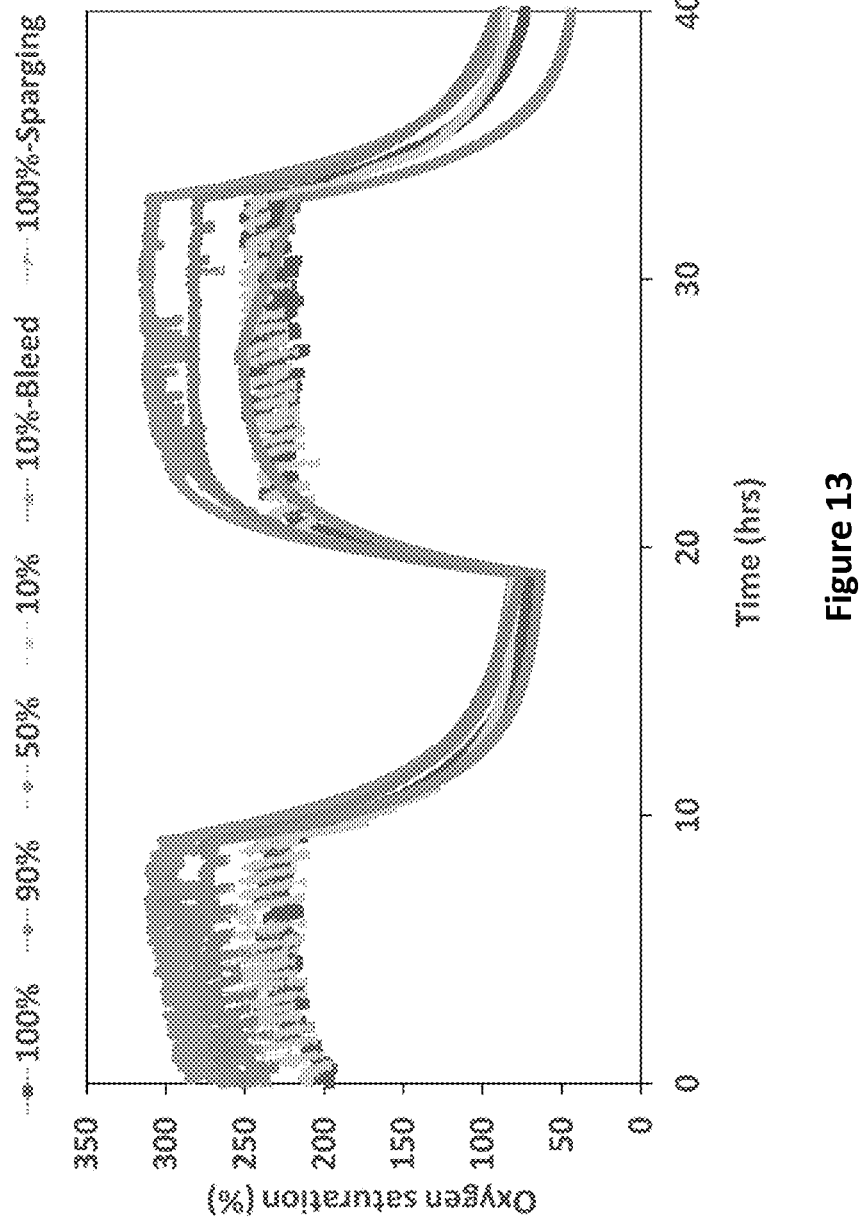
FIG. 13 illustrates dissolved oxygen levels were obtained during semi continuous operation with 3× phosphate amendment conditions.

FIGS. 12A and 12B shows that *Scenedesmus* biomass growth on all tested $CO_2$ concentrations was able to maintain a significantly similar productivity throughout the experiment. The growth productivity could be maintained at 0.06 g/L-d for 6-d SRT for batch and semi-continuous feeding with 3-fold phosphate amendment. Conventional sparging as a control showed the various $CO_2$ gas delivery by MC did not compromise their productivity. The factor affecting the productivity was the phosphate supply instead. Regular phosphate in BG-11 media did not sustain the biomass productivity within 6-d SRT operation, implying heterotrophic bacteria may compete with *Scenedesmus* for the limited phosphate resource. Therefore, 3-fold phosphate amendment could mitigate the competition and retrieve the productivity. The biomass productivities were not affected by high dissolved oxygen (DO) generated from photosynthesis, though various dissolved oxygen levels were obtained, i.e., 200% vs 300% from 100% and 50% $CO_2$, respectively (FIG. 13). The main DO difference was highly correlated with $CO_2$ gas mixed with air and venting frequency: pure $CO_2$ and high frequent venting (10% $CO_2$ with venting setup) did not lead to elevated DO levels. Less frequent venting (90% and 50% $CO_2$) and bleed operations drove more oxygen into the culture media.

Figure 14:
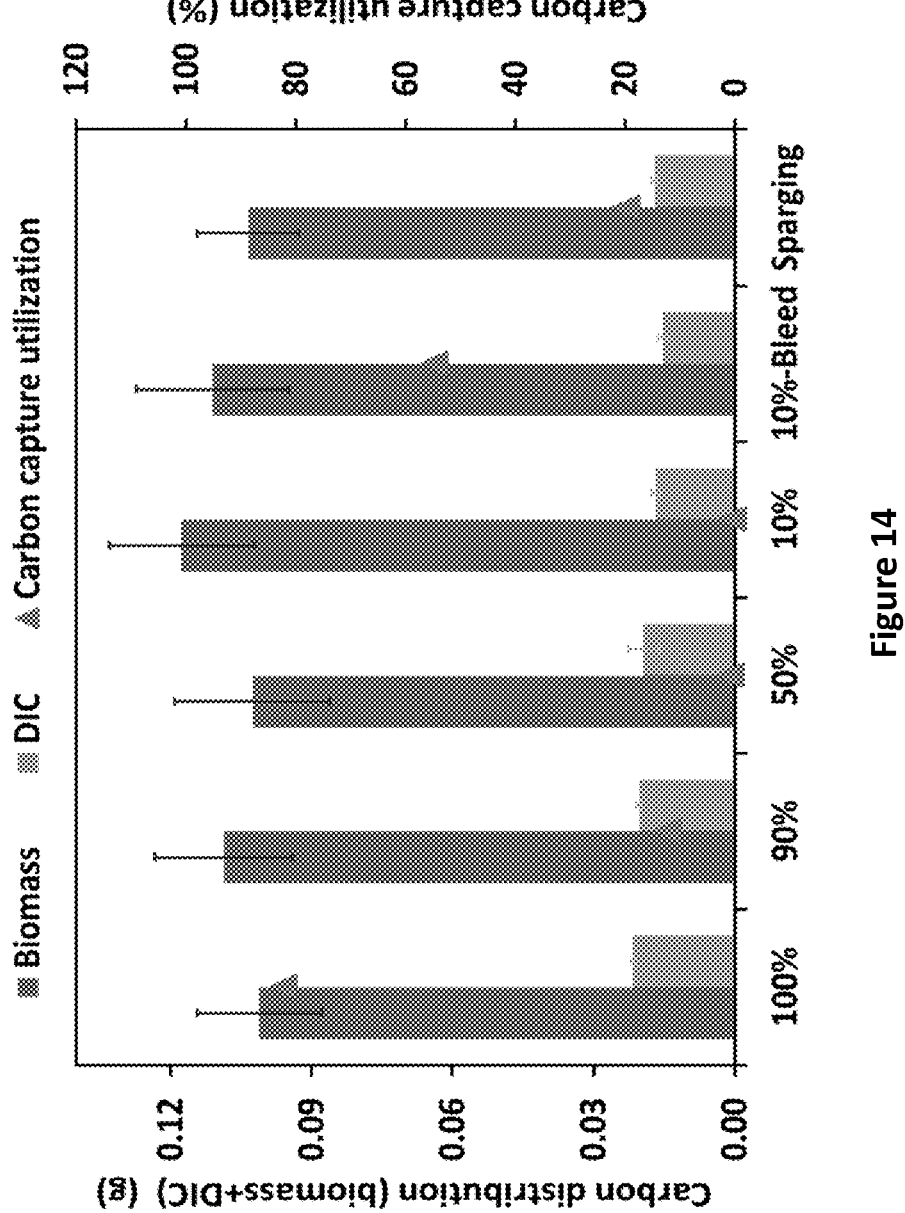
FIG. 14. Comparison of carbon distribution into biomass and dissolved inorganic carbon, along with the calculated carbon capture efficiency for different $CO_2$ concentrations. Net $CO_2$ added was obtained from the difference between feeding cycle and measured by DIC
Figure 15:
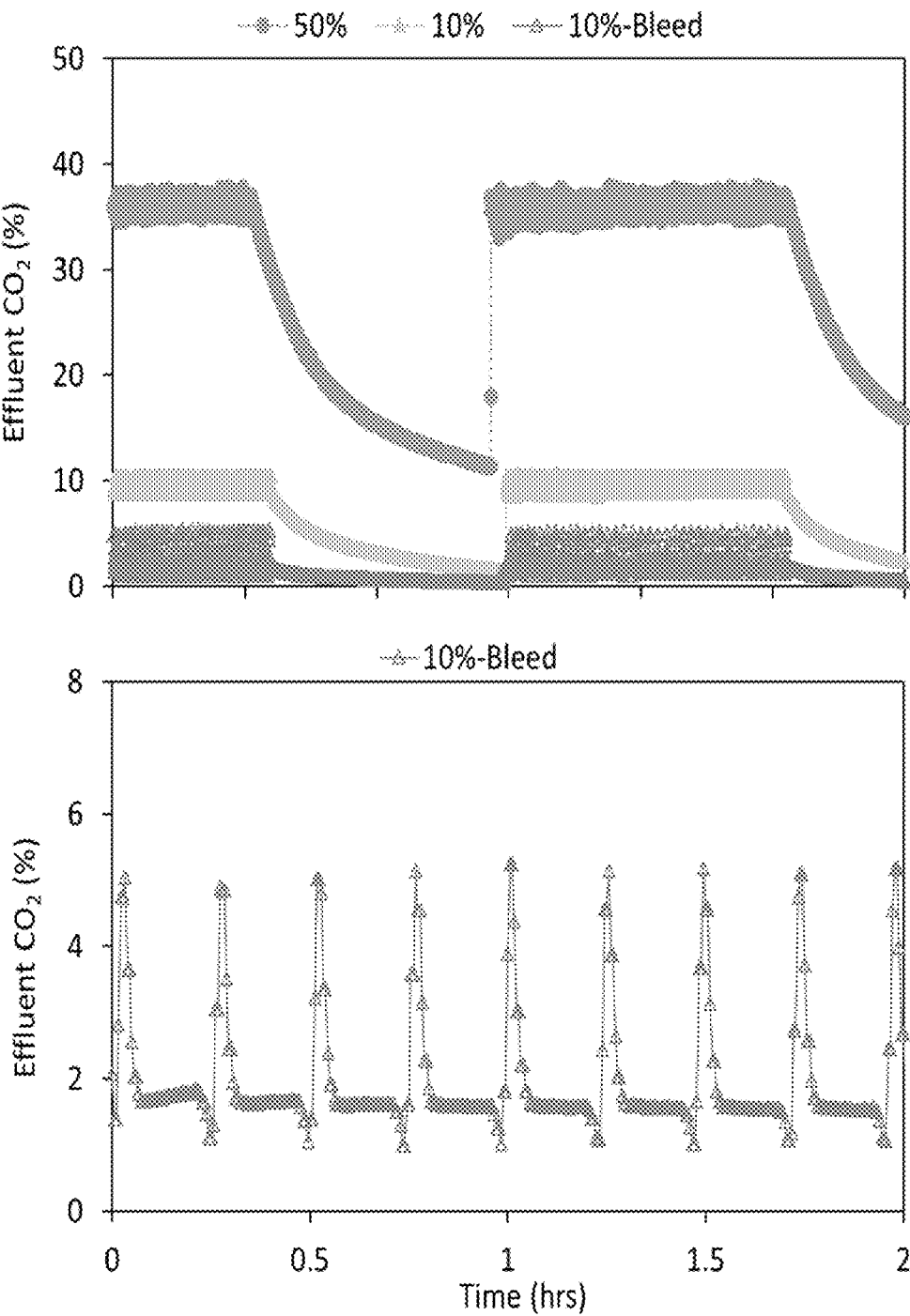
FIG. 15 illustrates effluent $CO_2$ exhausted from 50% and 10% $CO_2$ venting and 10% $CO_2$-bleed events.

FIG. 14 shows the distribution of delivered $CO_2$ into the biomass and DIC in the medium, along with carbon capture efficiency. The distributions of delivered $CO_2$ were almost the indistinguishable for each operating condition, because all systems had the same biomass-production rate and pH, which reinforced that the various forms of MC and sparging could support biomass growth when the pH was stabilized. Without any venting event, MC using 100% $CO_2$ gave nearly 100% carbon transfer efficiency but 82% CUE, which was far superior to the 20% efficiency with sparging. Delivering 10% $CO_2$ with the bleed-valve configuration gave a CUE of 60%, a significant improvement over sparging, but less than 100% $CO_2$. The CUE of 90%, 50% and 10% $CO_2$ with open venting were less than 15% of CUE. These low values were significantly lower than what should be expected. The reason for this was associated with small scale size (only 1.8 L) and no restrict of outflow rate. Due to not restricting the outlet flow, there was a significant amount of gas lost each time when the vent valve was opened. For example, FIG. 15 showed off-gas of 10% $CO_2$ was 10% and ~2% for venting and bleed operation, and their outflow rate was 1580 ccm and ~2 ccm, respectively given at 10 psig gas supply. Although ~12.5% $CO_2$ was captured by biomass cultivation from 50% $CO_2$, and much better than zero capture (fully ~50% $CO_2$ exhausted) with the abiotic venting, again, its high outflow rate dominated the $CO_2$ loss and resulted in poor CUE (<1%). Since the valve control was relayed on pH value, the loss was exacerbated by the relay setup, i.e., opening the vent valve required an increase in pH that created a time delay to flush out insert gas.

Figure 16:
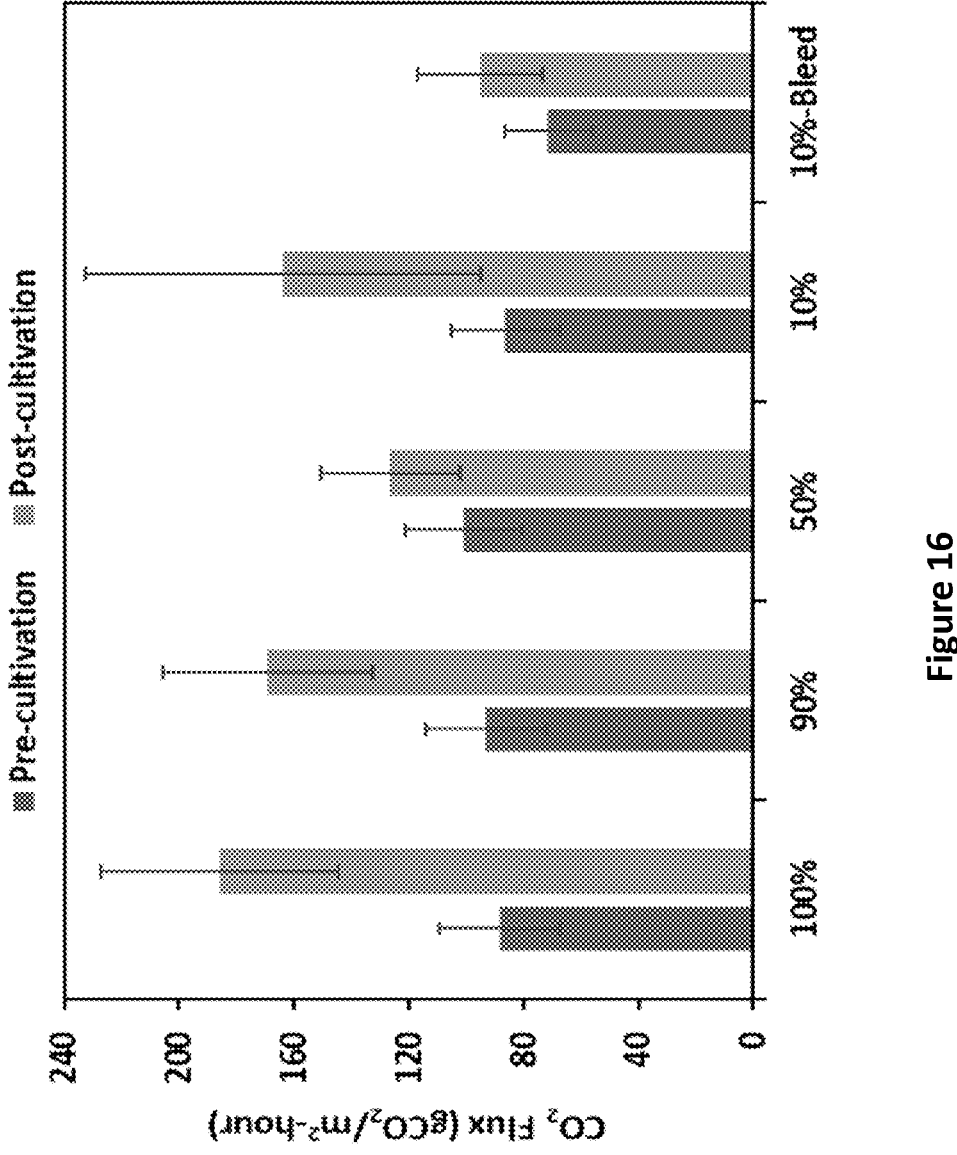
FIG. 16 illustrates the fiber bundle performance was reevaluated using 90% $CO_2$ with open-end scenarios (given 10 psig pressure supply) after 38-d cultivation.

Last, no significant flux decline with time was identified; to the contrary, their fluxes were even higher after the cultivation (FIG. 16). The possible reason could be porous size of inner fibers membrane was enlarged, since fiber membrane have been pressurized at 10 psig through the test. Therefore, MC approach is reliable for long-term usage.

Conclusion

Membrane carbonation (MC), which had been proven to be an alternative for delivering $CO_2$ without bubbling, captures nearly 100% of the $CO_2$ when supplying pure $CO_2$. However, most industrial $CO_2$ sources are composite gas mixtures with a $CO_2$ content ranging from 10% to 90%. All MC operating strategies gave the same biomass-production rate when the pH was stabilized at the same value. MC using 100% and 50% $CO_2$ gave nearly 100% transfer efficiency when a venting value was used, since the venting valve had to be opened infrequently. When delivering 10% $CO_2$, the bleed-valve configuration gave the best $CO_2$-capture efficiency, between 55 and 60%, which was a 3-fold increase compared to conventional sparging. The capture efficiencies for 50% $CO_2$ with a bleed valve and sparging was 50-65%. These lower capture efficiencies were associated with small-scale size of the system, and a larger system should allow the gas-outflow rate to be restricted more, which will improve efficiency.

Example 2

Improved $CO_2$-Transfer Efficiency Using Membrane Carbonation in Outdoor Raceways This Example illustrates $CO_2$ transfer efficiency can be improved using membrane carbonation in outdoor raceways. This Example illustrates the following: (1) membrane carbonation can be used to ensure high $CO_2$ transfer efficiency; (2) using MC increased carbon utilization efficiency by 2.5 to 3-fold higher than sparging; (3) growth on ammonium and nitrate had a CUE of 106% and 67% at pH 8.5, respectively; and (4) MC is a viable technology for delivering $CO_2$ to algal culture.

Materials and Methods

Cultivation

All experiments were carried out using *Scenedesmus acutus* LRB-AP-0401 cultured in outdoor raceway ponds at the Arizona Center for Algae Technology and Innovation (AzCATI) field-site in Mesa, AZ. Experiments were completed in three raceway ponds, each with an area of 5.6 m², a total volume of 900 L, and an average cultivation depth of 16 cm. Cultures were grown using semi-continuous harvesting to maintain the culture in an active growth stage. The culture medium was based on BG-11 Medium utilizing all ingredients (except phosphate) at $\frac{1}{8}^{th}$ to $\frac{1}{4}^{th}$ the original strength, depending on the experiment. Because these experiments utilized tap water, additional magnesium sulfate, calcium chloride, and sodium carbonate were not added to the culture. Phosphate was double the concentration compared to the other ingredients; this relatively higher concentration was utilized to ensure that P limitation did not occur. To evaluate the effect of N source, sodium nitrate was replaced with ammonium bicarbonate in 2 of the 4 experiments. For $CO_2$ delivery, two of the raceways utilized membrane carbonation (MC), while one utilized sparging as a control.

Monitoring and Control
Temperature and pH

Temperature and pH were continuously monitored using a Neptune Apex controller (Neptune Systems, LLC), which also activated solenoid valves to deliver $CO_2$ when the pH of the culture exceeded 8.5 for experiments 1, 2, and 3 and 8.0 for experiment 4. Environmental conditions were measured with an Argus weather station capable of recording ambient temperature, relative humidity, and light intensity (Argus Control Systems, LLC.).

$CO_2$ Delivery $CO_2$ delivery for the control raceway was accomplished using the existing sparging modules at AzCATI, which are fine-bubble diffusers (Atlantic Diffusers, AB-70008) that produces a bubble size between 1-5 mm. For experiments 2, 3, and 4, the delivered $CO_2$ flow rate was controlled by a mass flow controller with a totalizing function (MC-20SLPM, Alicat Scientific, USA) set to a flow rate of 1400 sccm. The other 2 raceways utilized custom MC units, shown in FIGS. 3A-3B. The MC units were built using composite HFM (Model MHF 200TL, Mitsubishi-Rayon Co., Ltd., Japan) that consisted of a 1-μm-thick non-porous polyurethane core and macroporous polyethylene structural layers. Using laboratory experiments, Shesh et al. (*Journal of Membrane Science*, 592 (2019) 117389) showed that these HFMs provide efficient delivery of $CO_2$ into the liquid phase. The membranes were operated with 100% $CO_2$ at a pressure between 10 psig (69 kPa-gauge) and 16 psig (110 kPa-gauge). The design, shown in FIG. 3B, created a membrane curtain that was aligned parallel to the liquid flow; it imposed minimal restriction to the fluid flow. The membrane unit consists of ~1600 individual fibers with a total surface area of 0.56 m². As the systems were utilizing pure $CO_2$, the modules were operated in a closed-end mode, meaning that all $CO_2$ entering the MC diffused across the membrane into the medium, ensuring 100% transfer efficiency to the medium. For all experiments, one of the raceways containing MC (designated as MC1) utilized an Alicat flow totalizer (M-20SLPM, Alicat Scientific, USA) to track $CO_2$ delivered to the module. MC2 did not have a flow totalizer.

Biomass Density

Ash-free dry weight (AFDW) was measured in triplicate to assess growth performance. Glass-fiber filters (VWR 696 glass microfiber 1.2 μm) were ashed for 4 hours at 500° C. prior to initial weighing. Triplicate samples were collected by filtering 10 to 20 mL per filter (depending on culture density). Samples were placed into an oven at 60° C. overnight. The filters with biomass were weighed to determine dry cell weight and then ashed at 500° C. for 4 hours, cooled, and reweighed to determine the AFDW of the biomass.

Calculating Areal Productivity During Batch Growth

Volumetric productivity during batch growth was calculated by subtracting consecutive AFDW concentrations and dividing the mass producing by the elapsed time. To convert volumetric productivity to areal productivity, the volumetric productivity was multiplied by the culture volume of 900 L (0.9 m³) and divided by the raceway surface area of 5.6 m².

Carbon Utilization Efficiency

Carbon utilization efficiency (CUE) was calculated based on the amount of $CO_2$ delivered, as measured by the totalizers, and the estimated amount of $CO_2$ incorporated into the algal biomass by algal growth. The carbon content of the algal biomass was approximately 52% (provided by AzCATI using CHN analysis). To determine the total carbon consumed, the volumetric productivity (g-biomass·m⁻²·d⁻¹) was multiplied by the total volume of the raceway (900 L), the carbon fraction of the biomass (0.52 g-carbon·g-biomass⁻¹), and the molar ratio of C to $CO_2$ (12 g C/44 g $CO_2$). CUE was then calculated by dividing g-$CO_2$ contained in biomass by g-$CO_2$ delivered and multiplying by 100 to represent a percentage. For cultivation on ammonium bicarbonate, the algal biomass had an additional source of inorganic carbon available. To account for the carbon attributed to the DIC in added ammonium bicarbonate, the AFDW of the culture was multiplied by the nitrogen content from the provided CHN analysis. It was assumed that 1 mole of ammonium uptake from ammonium bicarbonate would provide 1 mole of carbon to the biomass, or about 20% of the C uptake to synthesize new biomass. This produces a net CUE for the carbon incorporated from $CO_2$ and provides a value for comparison with cultures grown on nitrate.

Fiber Performance

To track fiber performance, i.e., $CO_2$ flux through the membrane (g-$CO_2$·$m^{-2}$-fiber SA·$d^{-1}$), the amount of $CO_2$ delivered per day, as measured by the Alicat totalizer, was divided by the amount of time the $CO_2$ valve was open and divided by the surface area of the MC.

Results and Discussion

Growth on Nitrate

Figure 17:
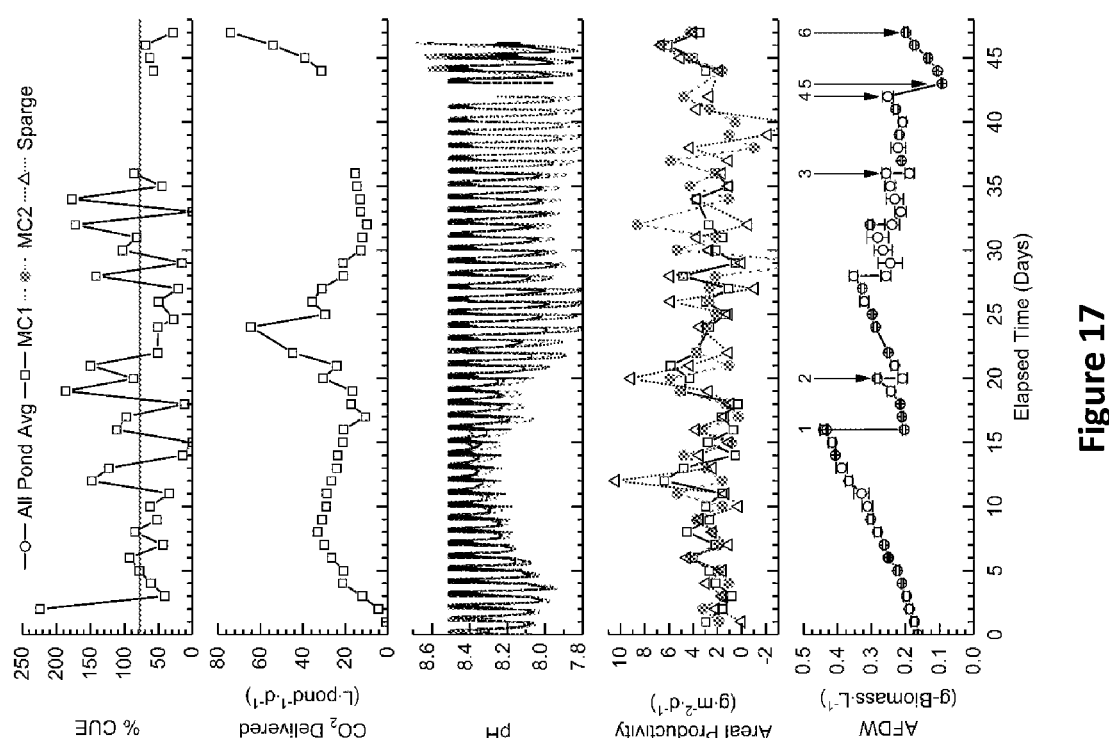
FIG. 17 shows CUE, $CO_2$ delivery, pH, Areal productivity, and AFDW (Ash-Free Dry Weight) for cultures from various experiments. Only MC1 was monitored for $CO_2$ delivery and CUE due to limited flow-controller availablity. The horizontal line in the % CUE graph represents the average CUE for the experiment.
Figure 18:
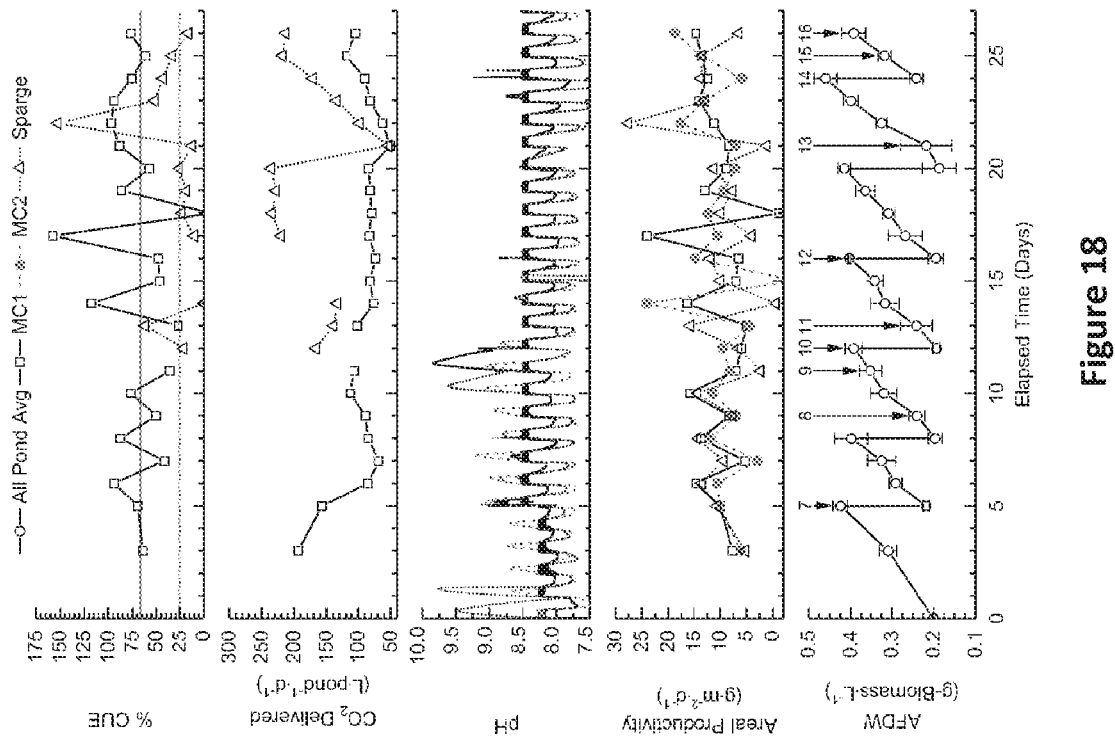
FIG. 18 shows CUE, $CO_2$ delivery, pH, Areal productivity, and AFDW for cultures from various. MC1 and sparging were monitored for $CO_2$ delivery to calculate CUE. The horizontal lines in the CUE graph represents the average CUE for the experiment.

Two experiments were conducted using sodium nitrate as the nitrogen source and with semi-continuous harvesting. Table 2 provides information related to notable events during the experiments, including percent harvested, culture crashes, and other special circumstances. FIG. 17 shows AFDW, areal productivity, pH, $CO_2$ delivery, and % CUE for cultures from Experiment 1, while FIG. 18 provides the same information for Experiment 2.

During experiment 1, the $CO_2$ delivered to raceway MC1 was recorded by the totalizer and documented at each sampling point. This was combined with the daily biomass productivity to determine the CUE. Due to the normal variabilities in AFDW and biomass productivity, the daily CUE fluctuates significantly. The average CUE for Experiment 1 was 78±55%. These results are consistent with, although superior to, those of de Godos, et al. (*Bioresource Technology*, 153 (2014) 307-314), who reported that algal growth on nitrate had a CUE of 66%, when they were able to transfer 90% of the delivered $CO_2$ into the culture medium. CUE was not measured for sparging during experiment 1.

As Experiment 2 was conducted during the spring months, the average biomass productivity was higher, 10.2±3.6 g·$m^{-2}$·$d^{-1}$. Although productivities had variability from day to day, the averages were similar for sparging and MC. About halfway through experiment 2, $CO_2$ delivery into the raceway containing the sparger module was tracked and it was continued to be tracked if for MC1. The average CUE for the experiment for MC1 and sparger were 67±35% and 25±18%, respectively. Thus, the CUEs for MC1 were significantly higher than for sparging. Putt et al. (*Bioresource Technology*, 102 (2011) 3240-3245) showed that sparging was able to achieve a delivery efficiency into the medium of 37% using a bubble size of 3 mm at a depth of 15 cm. However, those authors were sparging into water spiked with NaOH to a pH of 10, which created an environment with a very large carbon deficiency that artificially increased the $CO_2$ transfer efficiency. Based on numbers from de Godos, et al. (*Bioresource Technology*, 153 (2014) 307-314) that biomass can capture approximately 73% of delivered $CO_2$, the delivery of 37% $CO_2$ would translate to a CUE of 27%, which is comparable to the CUE calculated for sparging in this experiment.

TABLE 2

Description of notable events that occurred during experimentation and correlate to specific points on FIGS. 17 and 18.

| Experiment Event Date | Elapsed Time (days) | Event Note |
|---|---|---|
| 1 | 16 | Started Semi-continuous operation. Harvested 50% of the biomass. Supplied ⅛ BG-11 for total culture volume. |
| | 20 | Reduced harvest amount from 50% to 25%. |
| | 36 | MC1 culture lost during harvesting process. |
| | 42 | Culture crash imminent. MC2 and Control filtered to 50 µm and combined in separate raceway for bleaching. |
| | 43 | Culture restarted in MC1, MC2 and Control. |
| | 47 | Experiment stopped due to significant contamination concerns. |
| 2 | 6 | Semi-continuous operation. Harvested 50% of the biomass. Supplied ⅛ BG-11 for total culture volume. |
| | 9 | MC1 multiple fibers cut by wild animal (raccoon). |
| | 11 | MC1 removed for repair. |
| | 12 | MC1 still has small leaks. |
| | 13 | Replaced MC1 and MC2 with new modules. Decreased operating pressure from 110 to 69 kPa-gauge. |
| | 15 | Sparger gouged by wild animal (raccoon). Repaired with temporary patch. |
| | 21 | Sparger replaced with new module. Significant contamination developing. |
| | 24 | Increased nutrient supply to ¼ BG-11 for total volume. |
| | 25 | Increased pressure from 69-110 kPa-gauge. |
| | 26 | Experiment ended due to contamination. |

Growth on Ammonium Bicarbonate

Figure 19:
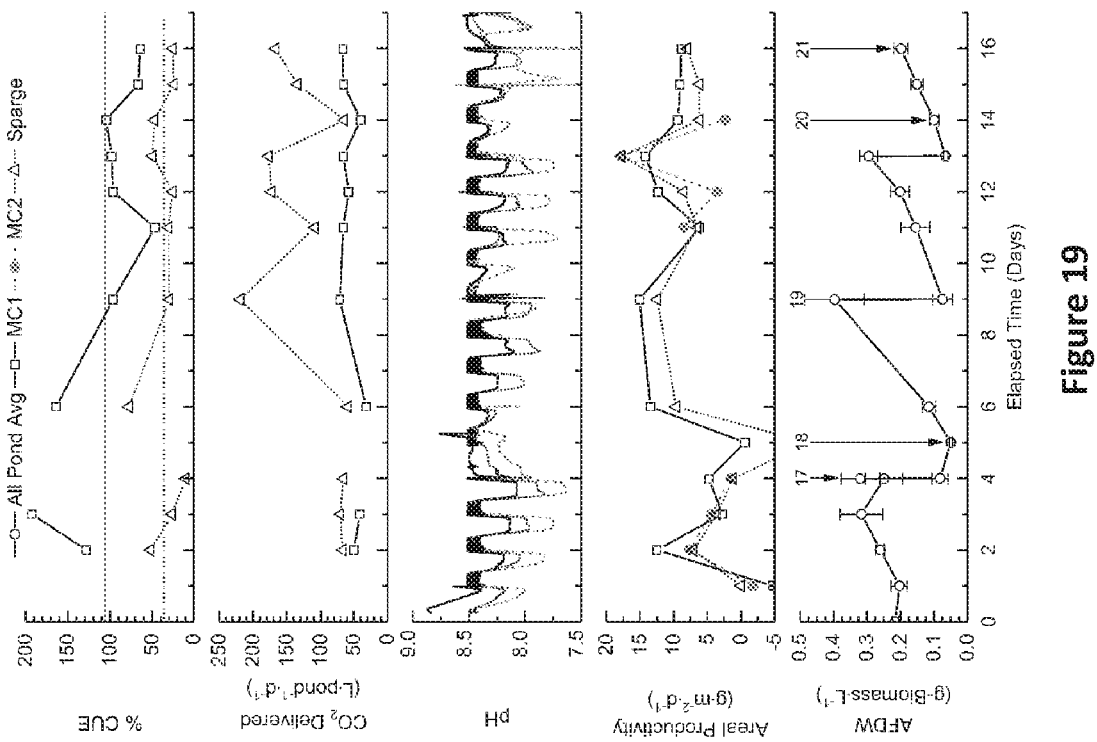
FIG. 19 shows CUE, $CO_2$ delivery, pH, Areal productivity, and AFDW for cultures from various studies. MC1 and sparging were monitored for $CO_2$ delivery to calculate CUE. The horizontal line in the % CUE graph represents the average CUE for the experiment.
Figure 20:
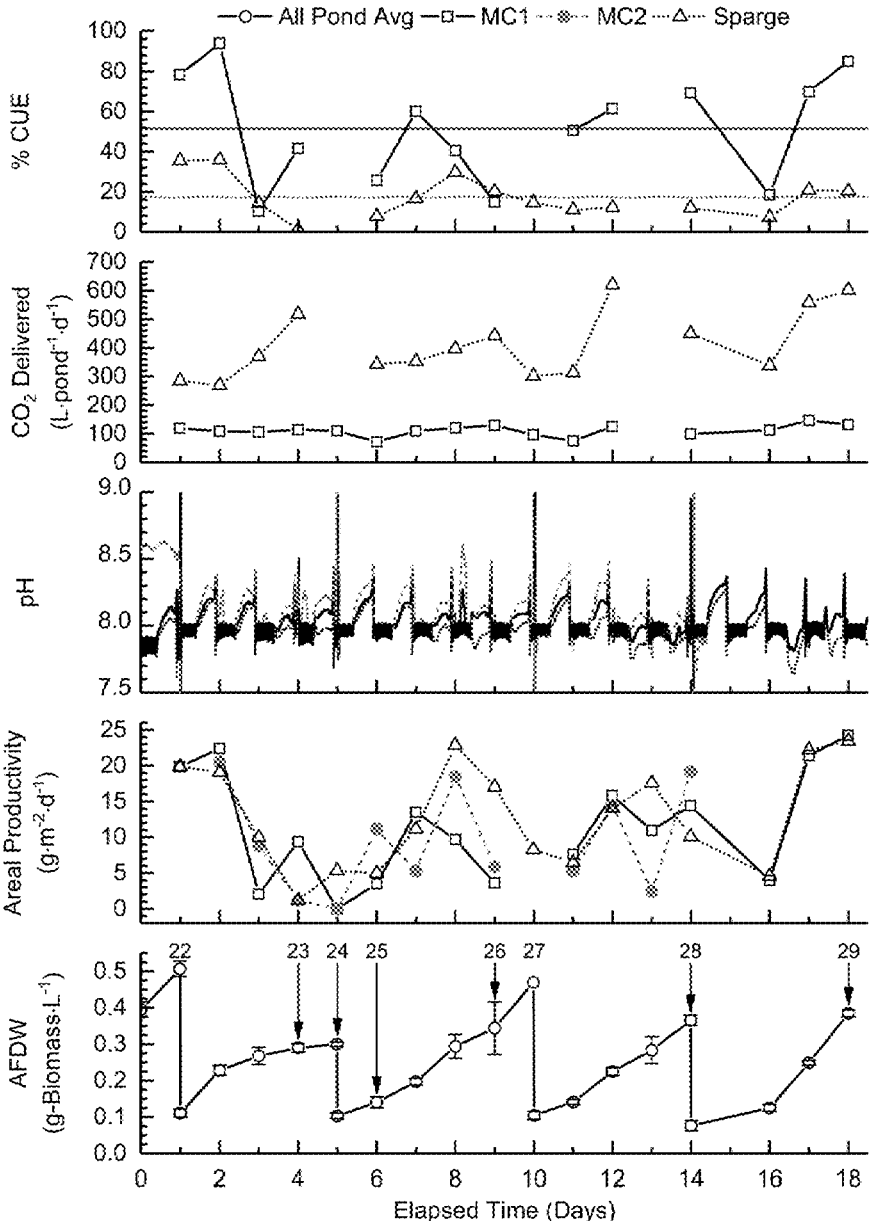
FIG. 20 shows CUE, $CO_2$ delivery, pH, Areal productivity, and AFDW for cultures from various experiments. MC1 and sparging were monitored for $CO_2$ delivery to calculate CUE. The horizontal line in the % CUE graph represents the average CUE for the experiment.

Two experiments were conducted using ammonium bicarbonate as the nitrogen source and with semi-continuous harvesting. Table 3 provides information related to notable events during the experiments, including percent harvested, culture crashes, and other special circumstances. FIG. 19 shows AFDW, areal productivity, pH, $CO_2$ delivery, and % CUE for cultures from Experiment 3, while FIG. 20 provides the same information for Experiment 4.

Experiment 3 was conducted with a pH setpoint of 8.5, the same setpoint as for Experiments 1 and 2. One challenge with using a pH of 8.5 is that it allows more than 10% of the total ammonia to be in the form of free ammonia. This equates to more than 0.4 mM free ammonia, which has been documented to cause ammonia toxicity. The combination of ammonia toxicity with high light intensity in dilute cultures led to culture loss of MC2 and a decrease in biomass concentrations in MC1 and the sparged raceways, as shown by Events 17 and 18 in FIG. 19. However, the biomass was able to recover, and the biomass productivity for the experiment was 6.7±6.0 g·$m^{-2}$·$d^{-1}$. The main improvement for the experiment was the increase in CUE, which was 106±45% and 36±19% for MC1 and sparged systems, respectively. The ability of the MC1 culture to achieve greater than 100% CUE was due to the pH setpoint being slighlty higher than the equilibrium pH of the culture. This can be seen by the decrease in pH at night from 8.5 to ~8.2 (FIG. 19). The higher pH during the day created a carbon-negative environment that pulled $CO_2$ from the atmosphere, in addition to the supplied $CO_2$.

The effects of $CO_2$ addition from the atmosphere is reinforced by the result of Experiment 4, where the pH setpoint was reduced to 8.0 to decrease ammonia toxicity. That the pH setpoint was lower than the equilibrium pH is demonstrated by the increase in pH at night, caused by $CO_2$ off-gassing, and confirmed by the decrease in the CUE to 51±27% and 17±10% for MC1 and sparged, systems, respectively.

TABLE 3

Description of notable events that occurred during experimentation and correlate to specific points on FIGS. 19 and 20.

| Experiment Event Date | Elapsed Time (days) | Event Note |
|---|---|---|
| 3 | 4 | Harvested 75% of the culture. Supplied ¼ BG-11 for the total volume. Cultures were supplied with ammonium bicarbonate instead of sodium nitrate. |
| | 5 | Low biomass concentrations, ammonia toxicity, and high light intensity caused a decrease in AFDW. MC2 did not recover. |
| | 9 | Harvested 75% of the culture. MC1 biomass was used to restart MC2 raceway. |
| | 14 | MC-2 culture crashed due to contamination. |
| | 16 | Experiment ended due to contamination. |
| 4 | 1 | Harvested 75% of the culture from MC1 and sparging, and inoculated MC2. pH Setpoint is at 8.0 to reduce ammonia toxicity. |
| | 4 | Holes in sparger from wild animal (raccoon). Temporary repair. |

TABLE 3-continued

Description of notable events that occurred during experimentation and correlate to specific points on FIGS. 19 and 20.

| Experiment Event Date | Elapsed Time (days) | Event Note |
|---|---|---|
| | 5 | Harvested 80% of the culture. |
| | 6 | Replaced sparger unit. |
| | 9 | MC1 and MC2 crashed due to contamination. |
| | 10 | Harvested 80% of sparging culture. Used 40% to restart MC1 and MC2. |
| | 14 | MC1 and sparging starting to crash. Replaced biomass with harvested biomass from MC2. MC2 did not recover. |
| | 18 | Experiment ended due to culture crash. |

Fiber Performance

Table 4 provides a summary of key results from the 4 experiments, including an evaluation of the $CO_2$ flux of the MC units at different points throughout each experiment. A major shift in flux occurred during Experiment 2. At event 11, the MC units were replaced with newly built modules. For the second round of prototypes, the manufacturing methods were improved so that the number of fibers that had become plugged during gluing was reduced. This improvement increased the flux of $CO_2$ per installed surface area.

TABLE 4

Summary of key results from experiments. Average values ± S.D. Initial and final flux are averages of the first and final 3 days, respectively.

| | Experiment 1 | Experiment 2[a] | Experiment 3 | Experiment 4 |
|---|---|---|---|---|
| pH Setpoint | 8.5 | 8.5 | 8.5 | 8.0 |
| Average temp (° C.) | 13.5 ± 3.1 | 17.6 ± 4.3 | 20.3 ± 4.8 | 23.1 ± 5.1 |
| Average Light ($kWh \cdot m^{-2} \cdot d^{-1}$) | 4.4 ± 1.1 | 6.2 ± 0.7 | 7.2 ± 0.8 | 8.3 ± 0.3 |
| Nitrogen source | Nitrate | Nitrate | Ammonium bicarbonate | Ammonium bicarbonate |
| Biomass Productivity ($g \cdot m^{-2} \cdot d^{-1}$) | 2.96 ± 1.92 | 10.19 ± 3.64 | 6.68 ± 6.01 | 11.76 ± 6.88 |
| MC Pressure (kPa-gauge) | 110 | 69-110 | 110 | 110 |
| Fiber SA ($m^2$) | 0.56 | 0.56 | 0.56 | 0.56 |
| Initial fiber flux ($g\text{-}CO_2 \cdot m^{-2} \cdot d^{-1}$)[b] | 860 ± 60 | 1100 ± 170 | 2600 ± 1100 | 1760 ± 380 |
| Final fiber flux ($g\text{-}CO_2 \cdot m^{-2} \cdot d^{-1}$)[b] | 630 ± 100 | 2890 ± 185[c] | 2430 ± 110 | 2600 ± 470 |
| Average fiber flux ($g\text{-}CO_2 \cdot m^{-2} \cdot d^{-1}$)[b] | 775 ± 120 | 1480 ± 660 | 2220 ± 750 | 2290 ± 610 |
| CUE MC1 | 78 ± 55% | 67 ± 35% | 106 ± 45% | 51 ± 27% |
| CUE Sparging | — | 25 ± 18% | 36 ± 19% | 17 ± 10% |

[a]Experiment 2 had the original MC module replaced after having several fibers cut by a raccoon.

[b]The area referenced in the membane flux is the total surface area of the fibers.

[c]Average for final 2 days only, after increasing to 110 kPa-gauge

Conclusion

MC, the bubbleless delivery of $CO_2$ through HFMs, was successfully integrated into outdoor raceways (5.6 m², 900 L) and operated continuously for up to 45 days. Biomass productivity associated with MC delivering $CO_2$ for pH control was comparable to cultivation using bubble sparging. The major difference in using MC and sparging with 100% $CO_2$ was the carbon utilization efficiencies (CUE), which was 3-fold higher for MC than sparging. Furthermore, the nitrogen source and pH setpoint affected the maximum achievable CUE.

Example 3

Evaluation of Co-Culturing *Chaetoceros* and *Pleurochrysis* Using Different Silicate Concentrations This Example demonstrates the following: *Chaetoceros* has an inhibitory effect on the *Coccolithophore pleurochrysis*; (2) *Chaetoceros* was consistently the dominant organism in co-culture cultivation, regardless of silicate concentration; (3) in 0.2 and 0.02 mM silicate, low levels of *Pleurochrysis* increased cell counts and biomass productivity of the co-culture; and (4) reducing silica decreases *Chaetoceros* specific growth rate, but biomass productivity did not change.

Microalgal cultivation has received significant attention for the ability to produce biofuels and become carbon neutral. However, there are several species of algae capable of carbon sequestration via calcium carbonate production that can push algal biofuels to become a carbon negative endeavor (Borowitzka, 1982). Coccolithophores are a subset of Haptophytes that produce protective scales (coccoliths) from calcium carbonate ($CaCO_3$) and can be used for sequestering $CO_2$ from the atmosphere (Brownlee and Taylor, 2004; Mohcimani and Borowitzka, 2006a). In addition, coccolithophorid algae can also produce high levels of lipids, which make them a potential target for renewable fuels and alternative food sources (Mohcimani and Borowitzka, 2006b; Moheimani and Borowitzka, 2012). While they're major contributors to biogenic calcification by producing calcium carbonate plates, they have a minor contribution to the total carbon fixation in marine ecosystems (Marsh, 2003; Raven and Giordano, 2009). However, by considering them for algal crop production, the amount of carbon fixation could significantly increase.

In traditional marine ecosystems, coccolithophores growth with other types of algae and organisms. One of the more common classifications of algae to be studied for biofuel production are diatoms. Diatoms are highly productive microalgae that accumulate substantially neutral lipids as triacylglycerol (TAG) that accounts for 25-45% of their dry weight which makes them attractive candidates as biofuel producers like green algae (Chisti, 2007; Aoyagi and Omokawa, 1992; d'Ippolito et al. 2015). They are also the world's largest contributors to biosilification that obligatory require silicate to regulate the growth and frustule formation (Kooistra et al. 2007; Pan et al. 1996).

Currently, significant research has shown that algal cultures will need value-added products to become economically feasible. Value-added products evaluate the ability to fractionate the biomass during biorefining to maximize the profitability of algal biomass. One of the most frequent areas of interest is high-value products such as omega-3 fatty acids and pigments (chlorophyll and carotenoids). Fucoxanthin is one of the most prominent light-harvesting carotenoid in diatoms and brown macroalgae, exhibit a characteristic brown color (Veith et al. 2009). Despite its food applications, studies have demonstrated that fucoxanthin may be used in numerous biological activities like anticancer, antiobese, antioxidant, anti-inflammatory, antidiabetic, antiangiogenic and antimalarial activities (Shannon and Abu-Ghannam, 2017; Bae et al. 2020). Compared to macroalgae, microalgae (diatoms) are usually rich in fucoxanthin under controlled conditions and considered as a good candidate for the mass production of fucoxanthin for commercial purposes (Kim et al., 2012). Among all macro and micronutrients, nitrogen, phosphorus, silicon, and iron are an important factor that regulates growth, pigments (chlorophyll and carotenoids) and lipid accumulation in diatoms (Fu et al. 2015; Kosakowska et al., 2004; Valenzuela et al., 2013).

Some nutrients especially nitrogen (N), phosphorus (P) and silicate (Si) regulates the production and storage of lipids in microalgae (Jiang et al. 2014). In diatom cells, silicate is limiting nutrient that alters or enhances growth rate and accumulation of lipid amount or inhibits DNA, protein, chlorophyll synthesis and cell division (Taguchi et al. 1987; Werner 1978; Martin-Jezequel et al. 2000). Under silicate-replete conditions, the growth rate of diatoms increases that favors diatom dominance over other phytoplankton species (Egge, 1998). When the other nutrients such as nitrate and phosphate are available in the environment, competition can be reduced with the fast-growing diatoms under low silicate conditions that contribute the coccolithophore bloom formations (Durak et al. 2016; Tyrrell and Merico, 2004). On the other hand, there are some evidences that diatoms which commonly represent more than 70% of the phytoplankton community at external silicate concentrations exceeding 2 mM, are always dominate the phytoplankton at high silicate concentrations (Egge and Aksnes, 1992). Egge and Aksnes (1992) reported that a common type of coccolithophore, *E. huxleyi* became dominant after 5 days under low silicate concentrations but at high silicate concentrations, it was out-competed by diatoms although, it was found in the initial community.

In natural environments the outcome of mixed-species competition has been determined by the performance in single-single experiments because of changeable nutrient status (Sterner and Elser, 2002; Litchman et al. 2007). There are limited information about the nutrients effects on co-culture of diatom and coccolithophore cells and their individual cultures in the literature (Zhao et al. 2015; Cermeño et al. 2011). To the best of our knowledge this is the first investigation to determine the influence of silicate nutrient on the growth of cultures by performing competitive experiments under different single diatom, coccolithophore and co-culture conditions. Pure culture of *Chaetoceros gracilis* was chosen as a representative of marine diatom because it can grow well under wide temperature range, including 15-35° C. (Chen et al. 2012). Also, it produces large amounts of fucoxanthin and lipids with faster growth rate (d'Ippolito et al. 2015). Furthermore, *Pleurochrysis carterae* was chosen as a representative of marine coccolithophore culture that can calcify without Si requirement (Durak et al. 2016). In this current study, *C. gracilis* (D), *P. carterae* (C) and their co-culture' (D&C) growth rate, productivity, ash content, yield of various photosynthetic pigments and lipid accumulation were analyzed under semi-continuous laboratory-scale cultivation with different silica contents. The results revealed that *C. gracilis* was consistently the dominant organism in co-culture cultivation, regardless of silicate concentration and silicate has an inhibitory effect on *P. carterae* in all cases.

2. Materials and Methods

2.1. Culture Conditions

Inoculums of *Chaetoceros gracilis* UTEX 2658, and *Pleurochrysis carterae* CCMP 647 microalgae obtained from the UTEX Culture Collection of Algae and Bigelow National Center for Marine Algae and Microbiota, respectively. Strains were cultivated in sterilized seawater with Defined Ocean Erdschrieber's Media (DIO-ESM). The content of the DIO-ESM media for 2N2P media was: 2 L (80 g instant ocean seawater), 4 mL $NaNO_3$, 4 mL $KH_2PO_4$ solution (37 Mm), 24 mL PIV Metal solution (1.5 g $Na_2EDTA$, 0.194 g $FeCl_3$ hexahydrate, 0.082 g $MnCl_2$ tetrahydrate, 0.01 $ZnCl_2$ anhydrous, 0.004 g $CoCl_2$ hexahydrate, 0.008 g $Na_2MoO_4$ dihydrate) 2 mL f/2 Vitamin Stock (10 mg thiamine hydrochloride, 100 μL of a 1 mg/mL biotin solution and 100 μL of a 1 mg/mL Vitamin B12 solution) and 20 μL $Na_2SeO_3$ (1 Mm). For 3N3P studies, $NaNO_3$, $KH_2PO_4$ and PIV Metal solution were added 2 times more to the 2 L media. After autoclaving (1 h, 121° C.) the media was enriched with sodium metasilicate ($Na_2SiO_3·9H_2O$, 6 g/200 mL) (Sigma-Aldrich). 500 mL glass wide mouth media storage bottles were used as photobioreactors with a working volume of 700 mL. $CO_2$ was delivered using non-porous hollow fiber membranes (HFMs) known as Membrane Carbonation (MC). For MC, bundles of HFMs were suspended in the reactors. The inlet of the bundles was installed with solenoid valves that controlled gas supply based upon a pH set point of 8.2 (FIG. 5A provides a schematic diagram of the system used for this Example). At the distal end of the bundles was a venting valve with a secondary pH set point of 8.25 to flush inert gases from membrane lumen, as the buildup of inert gases slows $CO_2$ transfer to the medium. Temperature and pH were monitored continuously using a Neptune APEX data logger.

The cultures were maintained by semi-continuously harvesting 50% (350 mL) of the culture every 3 days and replacing with fresh medium retaining a 6 day retention time. Samples were taken before and after harvesting every 3 days to measure ash free dry weight (AFDW), cell counts, pigment content (fucoxanthin, chlorophyll-a and chlorophyll-c), lipid content and calcium carbonate production. The cultures were incubated at 21±1° C. and grown on a 14 hours light: 10 hours dark cycle under 75 μmol photons/m2s light intensity at the culture surface provided by cool-white fluorescent bulbs.

2.2. Dry Weight, Ash-Free Dry Weight

Biomass, as total dry weight (DW), was determined by vacuum filtering (Rocker, MultiVac 310-MS) 20 mL of culture onto pre-weighed GF/F glass microfiber filters (Whatman GF/F, 47 mm, nominal pore size 0.7 μm) (before weighing the filters had been baked for 1 h at 500° C.). The filtered biomass was then washed with 20 mL 0.65 M ammonium formate solution to remove excess salts and dried at 80° C. for overnight and then placed in a desiccator for 1 h. After DW were measured, Ash free dry weight (AFDW) was determined by heating DCW samples to 500° C. for 1 h (Barnstead Thermolyne, 30400 Furnace) and then cooling 1 h in the vacuum desiccator before weighing (Zhu and Lee, 1997). To dissolve $CaCO_3$, filters were washed with 1 M HCl solution and dried at 80° C. for overnight again and then placed in a vacuum desiccator over silica gel for 1 hour. The weight of $CaCO_3$+Si (g) is calculated as;

$$(\text{Filter} + \text{biomass}) - (\text{Ashed filters}) \qquad (\text{Eq 1.})$$

The weight of $CaCO_3$ was calculated using the following equation:

$$CaCO_3(g/mL) = \{(\text{biomass} + \text{filter}) - \qquad (\text{Eq 2.})$$

$$(\text{acid washed filter})]/(\text{volume of sample})\} * 2$$

2.3.1. Productivity

Biomass productivity (BP) was calculated according to the Eq. (3) (Ra et al. 2015):

$$\text{Biomass Productivity} = (AFDW_F - AFDW_I)/t \qquad (\text{Eq 3.})$$

where $AFDW_F$ is the final dry biomass weight in mg/L, $AFDW_I$ is the initial dry biomass weight in mg/L and t is the cultivation time (3 days) comprised between final and initial measured expressed in days.

2.3. Cell Counts

Cell densities were determined using a Neubauer hemocytometer (Precicolor HBG, Germany) every three days under an Olympus BX51-P polarizing microscope. The chambers are 0.1 mm in height so that each square corresponds to a given volume, applied to count cells with a size of 2-30 μm and concentration of $10^4$-$10^7$ cells/mL. The concentration of cells was calculated following the method given by Guillard and Sieracki (2005) as following Eq (4):

$$\text{Cell density} = [(\text{Number of cells} \times 10000)/(\text{Number of squares})] \quad (\text{Eq 4.})$$

2.3.1. Growth Rate

*C. gracilis* and *P. carterae*'s growth rates were computed using the following Eq. (5) (Fogg and Thake, 1987):

$$\mu = (\ln N_t - \ln N_0)/t \qquad (\text{Eq 5.})$$

Where: μ is the specific growth rate (day-1), Nt is cell concentration at time t (cells/mL), $N_0$ is initial cell concentration at time 0 (cells/mL), and t is time (days).

2.4. Pigment Analysis

Pigment contents of the biomass were determined by using Varian 50 Bio UV-Visible spectrophotometer. 2 mL of culture was centrifuged for 10 minutes 10,000 rpm in a tube, the supernatant was eliminated and the pellet was extracted with 2 mL methanol (99.9%) after 10 minutes vortexing. The chlorophyll samples were wrapped with aluminum. Samples were centrifuged (10,000 rpm, 10 minutes) to remove cell debris before measurement. Absorption spectra were collected in the range 400-700 nm in a cell with a path length of 1 cm. Fucoxanthin pigment was measured and calculated at 470 nm wavelength. Chlorophyll-a (Chl-a) and Chlorophyll-c (Chl-c) concentrations were determined according to Eq. 6-7 of Ritchie (2006) for chlorophyll.

$$[Chl-a]\,\mu g/mL = -2.6839 \times (A630) + 13.2654 \times (A664) \qquad (\text{Eq 6.})$$

$$[Chl-c]\,\mu g/mL = 28.8191 \times (A630) - 6.0138 \times (A664) \qquad (\text{Eq 7.})$$

To obtain g-pigment/g-biomass, pigment concentrations were normalized with total biomass concentrations.

2.5. Fatty Acid Methyl Esters (FAMEs) Fatty Acid Determination

Figure 21:
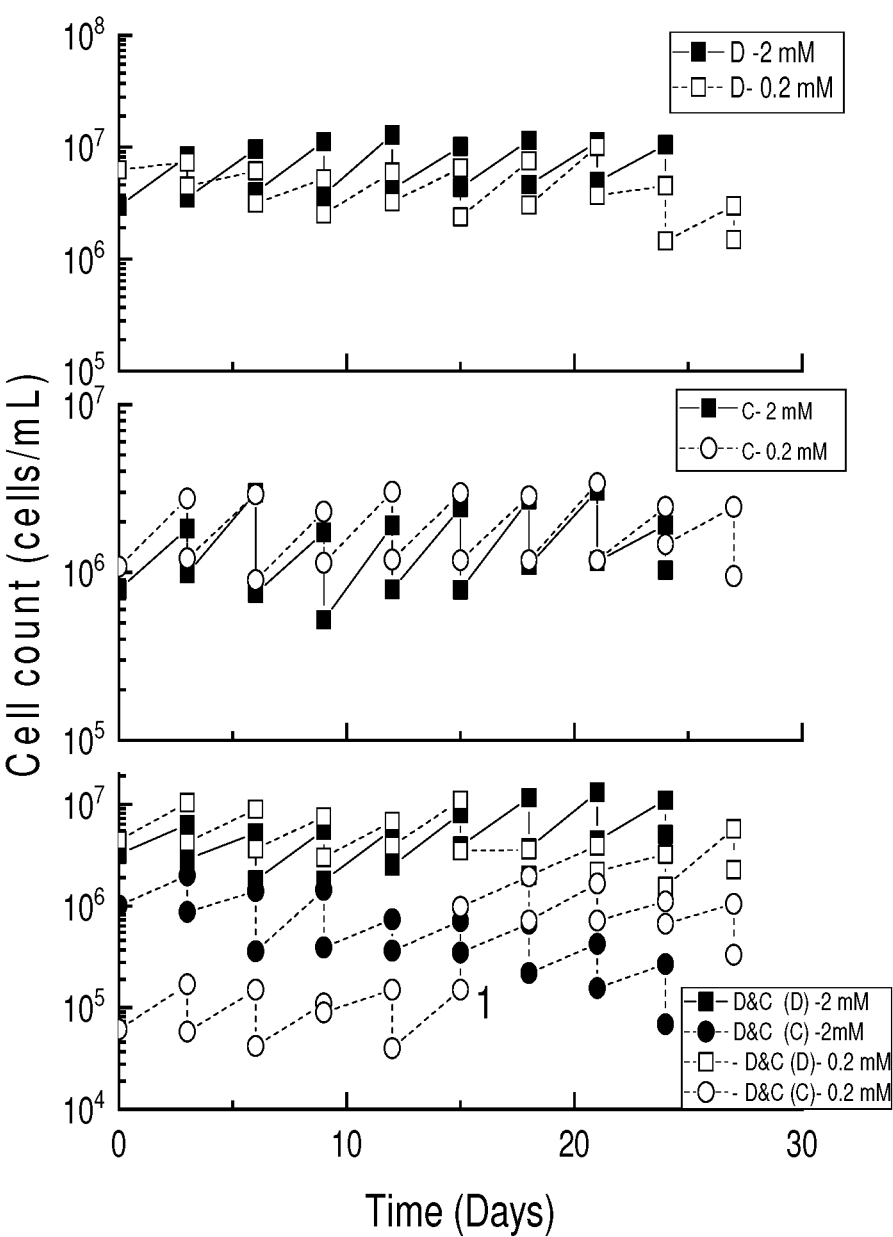
FIG. 21 shows cell counts for the marine algae (Top panel) *Chaetoceros gracilis* (D); (Middle Panel) *Pleurochrysis carterae* (C); and (Bottom panel) co-culture (D&C) at different silicate concentrations. (1-co-culture (D&C) was restarted at day 15 to increase the concentration of *P. carterae*.)

For fatty acid analysis, 10 mL of the culture sample was centrifuged at 4000 rpm in 15 minutes (Eppendorf, Centrifuge 5810 R). Then, supernatant was removed and remaining biomass was stored in the −20° C. freezer for overnight to ensure no water was visible. After the tubes were freeze-dried fatty acid methyl esters (FAMEs) were prepared by a modified acid transesterification with 2 mL of Methanolic-HCl were put into each tube and tubes were heated at 85° C. for 2.5 hours. 0.5 mL DI water, 1.55 mL Hexane were put into each tubes and tubes were vortexed. 1 mL of Hexane layer was put into the GC vials. The FAME composition was determined using an Agilent 7890A gas chromatograph (GC) and 5975C mass spectrometer (MS) (Agilent) with automatic injector (Agilent 7683B automatic liquid sampler) and DB-WAX capillary column (30 m×0.25 mm id). The quantities of individual FAMEs were identified and estimated from the retention time and peak areas on the chromatogram using authentic standards (Nu-Chek-Prep reference standard mix, GLC-68A).

gracilis (D) and a co-culture of the two organisms (C & D) grown with 0.2 and 2 mM silicate concentrations in semi-continuous cultivation. It can be clearly observed that silicate concentration is positively correlated with maximum cell counts of the monoculture C. gracilis strain during study period (FIG. 21, top panel). However, for single P. carterae, it appears that 2 mM that the highest concentration of silicate used given the cell counts were typically lower than those measured when 0.2 mM silicate was used (FIG. 21, middle panel). Accordingly, the increased silicate nutrient concentration increased C. gracilis' cell concentration while decreasing P. carterae' cell concentration. Moreover, as indicated in FIG. 21 (bottom panel), the cell count of P. carterae in co-culture decreased in all cases regardless of silicate concentrations.

Table 5 provides the average specific growth rates ($\mu$) and biomass productivity for semi-continuous culturing (6d HRT) for a minimum of 30 days for C. gracilis (D), P. carterae (C), C. gracilis in co-culture (D&C (D)) and P. carterae in co-culture (D&C (C)) under 0.2 and 2 mM silicate. 2 mM silicate was selected as the maximum concentration for growth, as silicate concentrations above 2 mM may result in polymerization, rendering the Si potentially less biologically available (Moll et al. 2014; Iler, 1979).

TABLE 5

Average growth rate, productivity, and ash content of C. gracilis (D), P. carterae (C) and co-culture (D&C) at different silicate levels. Error bars represent standard deviations in semi-continuous experiments.

| | | | Average Specific Growth Rate (day$^{-1}$) | AFDW Pre Harvest (g/L) | AFDW Post Harvest (g/L) | Average Productivity (g/L/d) | Average Ash Content (g/g) (%) |
|---|---|---|---|---|---|---|---|
| 2 Mm | D | | 0.322 ± 0.05 | 0.235 ± 0.02 | 0.104 ± 0.02 | 0.042 ± 0.005 | 38.70 ± 10.40 |
| (2 N 2P) | C | | 0.305 ± 0.08 | 0.207 ± 0.01 | 0.119 ± 0.02 | 0.027 ± 0.009 | 47.33 ± 10.89 |
| | D&C (Co) | D&C (D) | 0.333 ± 0.08 | 0.250 ± 0.01 | 0.123 ± 0.02 | 0.037 ± 0.006 | 43.37 ± 5.69 |
| | | D&C (C) | 0.205 ± 0.03 | | | | |
| 0.2 mM | D | | 0.259 ± 0.11 | 0.220 ± 0.02 | 0.095 ± 0.01 | 0.044 ± 0.004 | 35.99 ± 9.38 |
| (2 N 2P) | C | | 0.313 ± 0.02 | 0.191 ± 0.01 | 0.094 ± 0.02 | 0.034 ± 0.006 | 32.82 ± 3.29 |
| | D&C (Co) | D&C (D) | 0.262 ± 0.16 | 0.238 ± 0.01 | 0.109 ± 0.01 | 0.044 ± 0.007 | 38.11 ± 6.57 |
| | | D&C (C) | 0.191 ± 0.027 | | | | |
| 0.2 Mm | D | | 0.31 ± 0.046 | 0.221 ± 0.01 | 0.106 ± 0.01 | 0.041 ± 0.008 | 22.6 ± 5.56 |
| (3 N 3 P) | C | | 0.29 ± 0.058 | 0.188 ± 0.01 | 0.106 ± 0.01 | 0.034 ± 0.007 | 27.4 ± 2.10 |
| | D&C (Co) | D&C (D) | 0.31 ± 0.071 | 0.222 ± 0.01 | 0.120 ± 0.01 | 0.035 ± 0.010 | 20.7 ± 4.11 |
| | | D&C (C) | 0.20 ± 0.069 | | | | |

2.6. Statistical Analysis

Data analysis was performed using Minitab v.17 and the data was expressed as means±standard deviation (SD). The data under every treatment conformed to a normal distribution (Shapiro-Wilk, $p > 0.05$) and the variances could be considered equal (Levene's test, $p > 0.05$). One-way analysis of variance (ANOVA) with LSD post hoc tests for each parameter were performed on the growth rate, biomass productivity, pigment concentration, AFDW, ash % of DW for each treatment to assess the effects of silicate amount on growth and biochemical responses of D, C and D&C. To analyze two different cultures for same and different silicate amounts, independent two samples t-test were used as standard for statistical significance. Least significant difference was used to for post hoc analysis. P-values less than 0.05 were considered as statistically significant.

3. Results and Discussion 3.1. The Effect of Silicate Concentrations on Growth Rate and Biomass Productivity FIG. 21 shows the cell concentrations of the coccolithophore Pleurochrysis carterae (C), the diatom Chaetoceros As shown in FIG. 21 (top panel), single C. gracilis strain that was fed with 2 mM silicate exhibited higher cell concentrations compared with 0.2 mM silicate. As indicated in FIG. 21 (bottom panel), C. gracilis in co-culture with P. carterae, was consistently the dominant species in both 0.2 and 2 mM silicate concentrations influenced C. gracilis biomass and lower silicate concentration caused a decrease in growth to both individual and co-cultures of C. gracilis. Also, it is believed that decrease the silicate availability could increase the single growth of P. carterae based on the growth results presented here (Table 5).

In 2 mM cultures, the $\mu$ of the individual cultures of P. carterae (0.305±0.08 d$^{-1}$) and C. gracilis (0.322±0.05 d$^{-1}$) were similar, which is expected in semi-continuous cultures, where $\mu$ approximates the dilution rate of the culture of harvesting every 3 days (0.33 d$^{-1}$). However, $\mu$ of P. carterae in the co-culture was significantly lower according to one-way ANOVA with Tukey Pairwise test (p=0.003, $\alpha$=0.05), while C. gracilis showed minimal change. This means that P. carterae experienced either growth inhibition or competition in the presence of C. gracilis. However, based on the high level of nutrient supply, frequent harvesting, and no decrease in $\mu$ of *C. gracilis*, it appears unlikely that the cultures were competing for nutrients.

When the silicate was decreased to 0.2 mM, it was determined that the $\mu$ for the cultures and co-culture were not significantly affected, indicating that silicate was not a limiting nutrient during experimentation. However, the increased concentrations of silicate appeared to significantly reduce the biomass productivity of *P. carterae* from 0.034±0.006 g/L/d to 0.027±0.009 g/L/d (p=0.002, $\alpha$=0.05). As shown in Table 5, although nitrogen (N) and phosphorus (P) was increased from 2 N 2 P to 3 N 3 P with 0.2 mM silicate, biomass productivity didn't change significantly in *C. gracilis, P. carterae* and co-culture (F(2,22)=1.57, p=0.232, p>$\alpha$). *C. gracilis*'s biomass productivity was 0.04 g/L/d and harvesting period was 3 days. C:N:P ratio was 101:9:1 as MW and 38:4:1 as % wt (Mortensen et al. 1988). 2N/2 P (N (0.045 mM) and P (0.037 mM)) ratio could be calculated approximately 3 mM. It indicates that there are no nitrogen or phosphorus limitations in the media. However, in this study when the cultures media was changed from 2 N 2 P (0.313±0.02 day$^{-1}$) to 3 N 3 P (0.29±0.06 day$^{-1}$) with 0.2 mM Si, average specific growth rate of *P. carterae* in co-cultures was significantly different according to one-way ANOVA with Tukey Pairwise test (F(3,30)=14.55, p=0.000, p<$\alpha$). These indicate that *C. gracilis* was consistently the dominant organism in co-culture cultivation, regardless of silicate concentration and *C. gracilis* has an inhibitory effect on the *P. carterae* in co-culture.

Also shown in Table 5, the biomass productivity of the co-culture in 0.2 and 2.0 mM shows an insignificant decrease in productivity from 0.044±0.007 g/L/d to 0.037±0.006 g/L/d when increasing the silicate concentration (p=0.283, p>$\alpha$, $\alpha$=0.05). It was thought that higher silicate amount has a negative effect on single *P. carterae* strain that resulted with lower biomass productivity value in single *P. carterae* strain in 2.0 mM silicate compared to 0.2 mM silicate. In many calcifying systems, amorphous calcium carbonate (ACC) can crystallize and finally calcite precipitation occurs. It is known that some of coccolithophore strains such as *E. huxleyi* and *Pleurochrysis carterae* that lacks SIT (Silicate Transporters) or SITLs (SIT-like) in their genomes (Durak et al. 2016). Also, in Pleurochrysidaceae and Noelaerhabdaceae, requirement for Si in coccolithophore calcification may have been lost (Durak et al. 2016). Depend of these, in Si-depleted waters; Coccolithophores are able to outcompete Diatoms that can contribute to the formation of Coccolithophore blooms (Durak et al. 2016). Moreover, when *P. carterae* culture was dominant in co-culture in 3 N 3 P with 0.2 mM silicate, directly after inoculation of the two organisms, the average productivity was 0.029±0.011 g/L/d, but was replaced as the dominant organism by *C. gracilis* on day 21, which had an average biomass productivity of 0.041±0.001 g/L/d. Moreover, when the single strain *P. carterae* culture was fed with zero silicate 3 N 3 P media, biomass productivity of single strain was obtained as 0.034±0.006 g/L/d. These results also supported that single *P. carterae* culture grows better at low silicate levels and that silicate may play an inhibitory role on the growth of *P. carterae* culture. According to results that declared above, minimum silicate concentration was selected as 0.02 mM for *C. gracilis* analysis in this study.

3.2. The Effect of Silicate Concentrations on Organic Biomass and Ash Content

Dry weight is a significant parameter for estimating biomass concentration, productivity, and percentage of cell components, including both inorganic (e.g., minerals) and organic (e.g., sugars, lipids, proteins, and nucleic acids) contents of the sample, and the residual ash includes most of the inorganic content (Moll et al. 2014).

Figure 22:
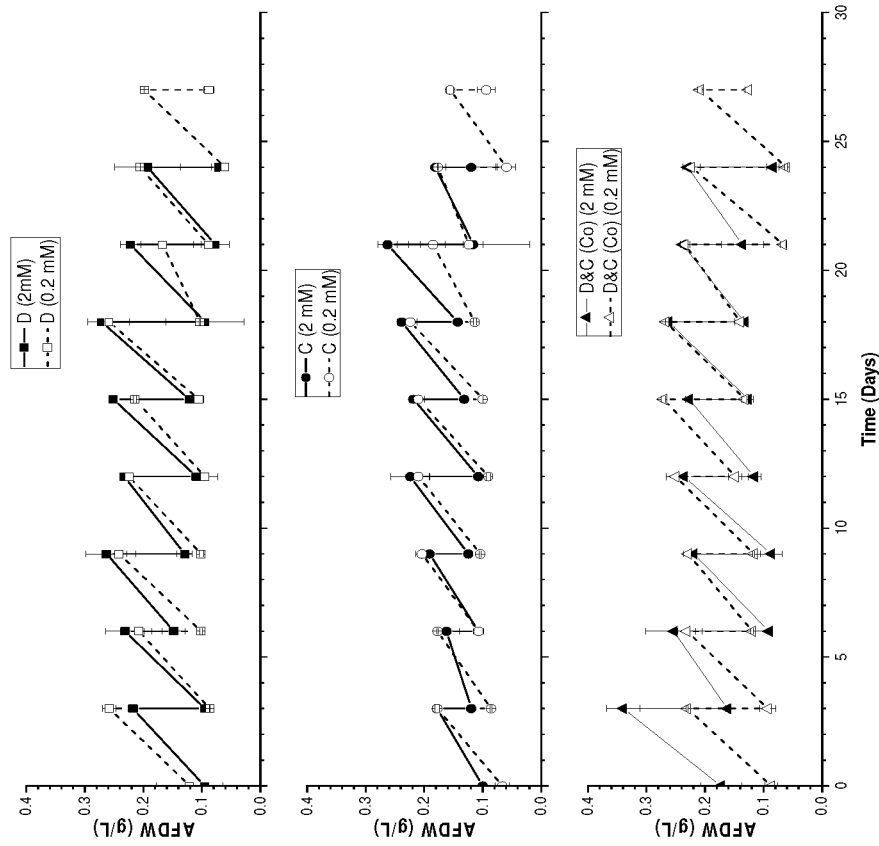
FIG. 22 shows a time course of Ash free dry weight (AFDW) of single marine algae (Top panel) Diatom (D) *Chaetoceros gracilis*, (Middle panel) Coccolithophore (C) *Pleurochrysis carterae*, and (Bottom panel) Co-culture (D&C) at different silicate levels.

FIG. 22 shows the ash free dry weight (AFDW) of the coccolithophore *Pleurochrysis carterae* (C), the diatom *Chaetoceros gracilis* (D) and a co-culture of the two organisms (C & D) grown with 0.2 and 2 mM silicate concentrations in semi-continuous cultivation. In this study, When AFDW of co-cultures were compared with each other for pre-harvesting exhibit higher performance in both 2 mM and 0.2 mM silicate concentration (F(2,23)=3.49, p=0.049, p<$\alpha$, $\alpha$=0.05) and (F(2,26)=8.60, p=0.002, p<$\alpha$, $\alpha$=0.05), respectively (Table 5). However, AFDW of *P. carterae* increased from 0.191±0.01 g/L to 0.207±0.01 g/L when silicate concentration increased from 0.2 mM to 2 mM silicate.

Ash content depends on the species and growth conditions and accounted for an average of 22-38% of the DW of *C. gracilis,* 27-47% of the DW of *P. carterae* and 20-43% of the DW of co-culture. Higher ash content of *C. gracilis* in this study at 2.0 mM Si indicated that cells of *C. gracilis* was highly silicified. Jiang et al. (2014) stated in their studies that as yet, no direct experiments have been carried out which confirm the increasing ash content of microalgae with the increased Si in the medium. However, in this study, ash content of single *P. carterae* and *C. gracilis* strains are higher under the highest concentration of Si (p<0.05) (Table 5). Especially for single *C. gracilis* strain, ash content varied from 29.17±4.95% to 38.70±10.40% when the silicate increased from 0.02 to 2 mM (F(3,30)=45.62, p=0.000, p<$\alpha$, $\alpha$=0.05).

3.3. Fatty Acid Composition, Lipid Productivities and Pigment Production in Response to Conditions in the Individual Cultures and Co-Culture.

Fucoxanthin is a fundamental pigment in diatoms whose function is to harvest light energy by associating with fucoxanthin-chlorophyll binding protein (Ban et al. 2006; Hashihama et al. 2010; Ishihara et al. 2015). Fucoxanthin has attractive attention due to its inhibitory effects on cancer cells and its antioxidant effect that make it a potential drug and dietary supplement similar to astaxanthin. (Hosokawa et al. 1999; Mori et al. 2004; Miki, 1991; Martin, 2015). Diatoms use solar energy to drive biosynthesis so they can be ideal biofactories for industrial fucoxanthin production (Tokushima et al. 2016). Chlorophyll-a is one of the dominant diatomaceous photosynthetic pigment and is purified from microalgae. Chls can be served as sensitizers for light-capturing materials in solar panels. Chlorophyll-c is a brown-yellow pigment that can be used as food colorant and for pharmaceutical purposes (Tokushima et al. 2016). In grown at 2.0 mM Si, the maximum fucoxanthin production was obtained at co-culture (F(2,5)=38.2, p=0.007, p<$\alpha$). All the fucoxanthin, Chl-a and Chl-c pigments were achieved higher amounts at co-culture than individual *C. gracilis* and *P. carterae* strains. It is believed that increasing of cell concentration is directly proportional with production of pigments by co-culture. Secondly, although fucoxanthin or Chl-a and Chl-c amounts didn't change substantially in single *C. gracilis* and co-culture, production of fucoxanthin and both Chls amounts increased from 2.0 to 0.2 mM Si. It also proves the silicate inhibition on individual *P. carterae* culture (Table 6).

Tokishima et al. (2016) stated in their studies that when cells were grown in F/2 enriched seawater under continuous light of 50 μmol photons/m$^2$s, Chl-a concentration reached 3.38 mg/L after 4 days of culture. At the same point, relative to Chl-a, amounts of Chl c1+2 and fucoxanthin by weight were ~20 and 60%, respectively. Over the next 4 days of culture, while cell density increased 1.6 fold, the Chl-a concentration decreased by 12%, 2.96 mg/L.

TABLE 6

Change in pigment production of *C. gracilis* (D), *P. carterae* (C) and co-culture (D&C) at different silicate levels. Error bars represent standard deviations in semi-continuous experiments.

| | | | Maximum fuxocanthin concentration (mg-pigment/ mg-biomass) | Maximum chlorophyll-a concentration (mg-pigment/ mg-biomass) | Maximum chlorophyll-c concentration (mg-pigment/ mg-biomass) |
|---|---|---|---|---|---|
| 2 Mm | D | | 41.81 ± 0.31 | 32.87 ± 0.18 | 6.62 ± 0.02 |
| | C | | 27.78 ± 0.02 | 29.97 ± 0.05 | 4.86 ± 0.02 |
| | D&C (Co) | D&C (D) | | | |
| | | D&C (C) | 57.14 ± 0.02 | 47.33 ± 0.01 | 8.82 ± 0.09 |
| 0.2 mM | D | | 43.92 ± 1.06 | 33.87 ± 0.80 | 11 ± 1.40 |
| | C | | 41.99 ± 0.52 | 38.09 ± 0.43 | 9.98 ± 0.78 |
| | D&C (Co) | D&C (D) | | | |
| | | D&C (C) | 44.91 ± 2.30 | 42.11 ± 1.75 | 13.63 ± 0.34 |

Chlorophyll-a per unit cell volume compared to non-limited cells increased, particulate silica per cell volume decreased (Harrison et al. 1977). However, in this study, production of Chl-a concentration remained same as 33.87±0.80 mg-pigment/mg-biomass from 2.0 to 0.2 mM Si.

REFERENCES FOR EXAMPLE 3

Borowitzka M A, Morphological and Cytological Aspects of Algal Calcification, International Review of Cytology, 1982, 74:127-162.

Paasche E, A review of the coccolithophorid *Emiliania huxleyi* (Prymnesiophyceae), with particular reference to growth, coccolith formation, and calcification-photosynthesis interactions Phycologia, 2002, 40, 503-529.

Moheimani N R, Webb J P, Borowitzka M A, Bioremediation and other potential applications of coccolithophorid algae: A review, Algal Research, 2012, 1(2):120-133.

Moheimani N R, Borowitzka M A, The long-term culture of the coccolithophore *Pleurochrysis carterae* (Haptophyta) in outdoor raceway ponds, Journal of Applied Phycology 2006a, 18:703-712.

Mohcimani N R, Borowitzka M A, Limits to Productivity of the Alga *Pleurochrysis carterae* (Haptophyta) Grown in Outdoor Raceway Ponds, Biotechnology and Bioengineering, 2006b, 96(1): 703-712.

Borowitzka M A. 1998. Limits to growth. In: Wong Y S, Tam N F Y, editors. Wastewater treatment with algae. Berlin: Springer-Verlag. p 203-226.

Veith, T., Brauns, J., Weisheit, W., Mittag, M., Büchel, C., 2009. Identification of a specific fucoxanthin-chlorophyll protein in the light harvesting complex of photosystem I in the diatom Cyclotella meneghiniana. Biochim. Biophys. Acta 1787, 905-912.

Shannon, E., Abu-Ghannam, N., 2017. Optimization of fucoxanthin extraction from Irish seaweeds by response surface methodology. J. Appl. Phycol. 29, 1027-1036.

Kim, S. M., Jung, Y.-J., Kwon, O.-N., Cha, K. H., Um, B.-H., Chung, D., Pan, C.-H., 2012. A potential commercial source of fucoxanthin extracted from the microalga Phacodactylum tricornutum. Appl. Biochem. Biotechnol. 166, 1843-1855.

Bae M, Kim M B, Park Y K, Lee J Y, 2020. Health benefits of fucoxanthin in the prevention of chronic diseases. Biochim Biophys Acta Mol Cell Biol Lipids. (in press).

Fu, W., Wichuk, K., Brynjólfsson, S. 2015. Developing diatoms for value-added products: challenges and opportunities. N. Biotechnol. 32, 547-551.

Kosakowska, A., Lewandowska, J., Stoń, J., Burkiewicz, K., 2004. Qualitative and quantitative composition of pigments in Phacodactylum tricornutum (Bacillariophyceae) stressed by iron. BioMetals 17, 45-52.

Valenzuela, J., Carlson, R. P., Gerlach, R., Cooksey, K., Peyton, B. M., Bothner, B., Fields, M. W., 2013. Nutrient resupplementation arrests bio-oilaccumulation in Phacodactylum tricornutum. Appl. Microbiol. Biotechnol. 97, 7049-7059.

Pérez L, Salgueiro J L, González J, Parralejo A I, Maceirasc R, Cancela Á. (2017) "Scaled up from indoor to outdoor cultures of *Chaetoceros gracilis* and *Skeletonema costatum* microalgae for biomass and oil production" Biochemical Engineering Journal, 127:180-187.

Roessler, P. G., 1988. Effects of silicon deficiency on lipid composition and metabolism in the diatom Cyclotella cryptica, Journal of Phycology 24, 394-400

Guillard R R, Sicracki M S. (2005) Counting cells in cultures with the light microscope. In: Anderson R A (ed) Algal culturing techniques, 1st edn. Academic Press, Elsevier, pp 239-252.

Ritchie, R. J. 2006. Consistent Sets of Spectrophotometric Chlorophyll Equations for Acetone, Methanol and Ethanol Solvents", Photosynthesis Research, Vol. 89:27-41.

Fogg G. E., Thake B. 1987. Algal Cultures and Ohytoplankton Ecology, 3r.d ed, The University of Wisconsin Press, USA.

Ra, C. H., Kang, C.-H., Jung, J.-H., Jeong, G.-T., Kim, S.-K., 2016. Enhanced biomass production and lipid accumulation of Picochlorum atomus using light-emitting diodes (LEDs). Bioresour. Technol. 218 (Supplement C), 1279-1283C.

Zhu, Y. Lee, Determination of biomass dry weight of marine microalgae, J. Appl. Phycol. 9 (1997) 189-194.

Y. J. S. Lai, E. Eustance, T. Shesh, G. S. Daprardar, E. Miranda, G. Orf, K. Redding, B. Rittmann, "Growth conditions affecting biomass competition for calcifying *Emiliania huxleyi* in a direct membrane-carbonation photobioreactor," ASU LightWork report, 2018.

Chen S-Y, Pan L-Y, Hong M-J, Lee A-C. The effects of temperature on the growth of and ammonia uptake by marine microalgae. Bot Stud. 2012; 53:125-33.

Cermeño P, Lee J-B, Wyman K, Schofield O, Falkowski P G. Competitive dynamics in two species of marine phytoplankton under non-equilibrium conditions. Marine Ecology Progress Series. 2011; 429:19-28.

Litchman E (2007) Resource competition and the ecological success of phytoplankton. In: Falkowski, Knoll A H (eds) Evolution of primary producers in the sea. Elsevier, Amsterdam, pp 351-375.

Sterner, R. W. & Elser, J. J. 2002. Ecological Stoichiometry: The Biol-ogy of Elements from Molecules to the Bio-sphere, 1st edn. Prince-ton University, Princeton, New Jersey, 464 pp.

Egge J K, Aksnes D L. Silicate as regulating nutrient in phytoplankton competition. Marine Ecology Progress Series. 1992; 83:281-289.

Tyrrell, T. & Merico, A. in Coccolithophores: From Molecu-lar Processes to Global Impact. (eds Thierstein, H. R. & Young, J. R.) 75-97 (2004).

Durak G M, Taylor A R, Walker C E, Probert I, de Vargas C, Audic S, Schroeder D, Brownlee C, Wheeler G L. A role for diatom-like silicon transporters in calcifying cocco-lithophores. Nature Communications. 2016; 7(1):1-12.

Egge J K. 1998. Are diatoms poor competitors at low phosphate concentrations? Journal of Marine Systems 16: 191-198.

Martin-Jézéquel V, Hildebrand M, Brzezinski M A. Silicon metabolism in diatoms: Implications for growth. Journal of Phycology. 2000; 36:821-840.

Werner D (1978) Regulation of metabolism by silicate in diatoms. In: Bendez G, Lindqvist I (eds) Biochemistry of silicon and related problems. Plenum, New York, pp 149-179.

Taguchi S, Hirata J A, Laws E A (1987) Silicate deficiency and lipid-synthesis of marine diatoms. J Phycol 23:260-267.

Raven, J. A. & Giordano, M. Biomineralization by photo-synthetic organisms: evidence of coevolution of the organisms and their environment? Geobiology 7, 140-154 (2009)

Marsh, M E. Regulation of $CaCO_3$ formation in coccolitho-phores, Comparative Biochemistry and Physiology Part B, Vol. 136, 2003, pp. 743-754

Westbrock, P., Brown, C. W., van Bleijswijk, J., Brownlee, C., Brummer, G. J., Conte, M., et al., 1993. A model system to biological climate forcing. The example of *Emiliania huxleyi*. Global Planet. Change 8, 27-46.

Pan Y, Subba Rao D V, Mann K H, Brown R G, Pocklington R. Effects of silicate limitation on production of domoic acid, a neurotoxin, by the diatom Pseudo-nitzschia mul-tiseries. I. Batch culture studies. Marine Ecology Progress Series. 1996; 131:225-233.

Kooistra WHCF, Gersonde R, Medina M, Mann D G. The origin and evolution of the diatoms: their adaptation to a planktonic existence. In: Falkowski P, Knoll A H, editors. Evolution of Primary producers in the sea. Burlington: Elsevier Academic Press; 2007. p. 207-49.

d'Ippolito G, Sardo A, Paris D, Vella F M, Adelfi M G, Botte P, Gallo C, Fontana A. Potential of lipid metabolism in marine diatoms for biofuel production. Biotechnol Bio-fuels. 2015; 8:28

Aoyagi K, Omokawa M. Neogene diatoms as the important source of petroleum in Japan. J Petrol Sci Eng. 1992; 7:247-62.

Tokushima H, Inoue-Kashino N, Nakazato Y, Masuda A, Ifuku K, Kashino Y. Advantageous characteristics of the diatom Chactoceros gracilis as a sustainable biofuel pro-ducer. Biotechnology for Biofuels. 2015; 9:235, 1-19.

Zhao Y, Wang Y, Quigg A. Comparison of population growth and phytosynthetic apparatus changes in response to different nutrient status in a diatom and a coccolithophore. J. Phycol. 2015; 15:872-884.

Moll K. M., Gardner R. D., Eustance E. O., Gerlach R, Peyton B. M. Combining multiple nutrient stresses and bicarbonate addition to promote lipid accumulation in the diatom RGd-1. Algal Research. 5:7-15.

Jiang Y., Laverty K. S., Brown J, Nunez M, Brown L, Chagoya J, Burow M, Quigg A Effects of fluctuating temperature and silicate supply on the growth, biochemi-cal composition and lipid accumulation of *Nitzschia* sp. Bioresource Technology. 2014; 154:336-344.

Tantanasarit C, Englande A. J., Babel S. Nitrogen, phospho-rus and silicon uptake kinetics by marine diatom *Chaeto-ceros calcitrans* under high nutrient concentrations. Jour-nal of Experimental Marine Biology and Ecology. 2013; 446:67-75.

Adeniyi O M, Azimov U, Burluka A. Algae biofuel: Current status and future applications. Renew Sustain Energy Rev 2018; 90:316-335.

Singh K, Kaloni D, Gaur S, Kushwaha S, Mathur G. Current research and perspectives on microalgae-derived bio-diesel. Biofuels 2017; DOI: 10.1080/ 17597269.2017.1278932.

Pires J C M. COP21: The algae opportunity? Renew Sustain Energy Rev 2017; 79:867-877.

Chisti Y. Biodiesel from microalgae. Biotechnol Adv 2007; 25:294-306.

UNFCCC, 2015 United Nations Framework Convention on Climate Change, Report of the Conference of the Parties on its twenty-first session, held in Paris from unfccc.int/ resource/docs/2015/cop21/eng/10.pdf [Jun. 2, 2019].

Shuba E S, Kifle D. Microalgae to biofuels: 'Promising' alternative and renewable energy, review. Renew Sustain Energy Rev 2018; 81:743-755.

IPCC SR1.5° C., 2018. Global Warming of 1.5° C. An IPCC Special Report on the Impacts of Global Warming of 1.5° C. Above Pre-industrial Levels and Related Global Greenhouse Gas Emission Pathways, in the Context of Strengthening the Global Response to the Threat of Cli-mate Change, Sustainable Development, and Efforts to Eradicate Poverty [V. Masson-Delmotte, P. Zhai, H. O. Pörtner, D. Roberts, J. Skea, P. R. Shukla, A. Pirani, W. Moufouma-Okia, C. Péan, R. Pidcock, S. Connors, J. B. R. Matthews, Y. Chen, X. Zhou, M. I. Gomis, E. Lonnoy, T. Maycock, M. Tignor, T. Waterfield (eds.)]. http:// www.ipcc.ch/report/sr15/.

Lin B., Raza M. Y. Analysis of energy related $CO_2$ emissions in Pakistan, Journal of Cleaner Production, 219 (2019), pp. 981-993.

Example 4

Synthesis Gas Delivery for Fatty Acids Production

Synthesis gas (or syngas) is produced at massive scale from variable sources, including biomass to atmospheric carbon dioxide. Syngas is a mixture of $H_2$, CO and $CO_2$, which makes it valuable as an alternative fuel. However, CO toxicity and $H_2$ flammability makes syngas dangerous to handle. The possibility to convert the gas to valuable liquid products is then attractive and has been widely explored.

Biologically conversion of syngas to liquid chemicals such as acids and alcohols has generated significant interest in the past few years, but a main challenge is having a bioreactor that allows high rates of gas delivery to the microorganisms. Homo-acetogens and chain elongators are the main groups of bacteria in the process, but both being anaerobic means that they are slow growers, making reten-tion a key element for process stability and high acid production[1]. Additionally, $H_2$ and CO have low water-solubility, with a Henry's constant of $7.7 \times 10^{-6}$ mol/m$^3$·Pa and $9.79 \times 10^{-6}$ mol/m$^3$·Pa respectively, compared to $3.4 \times$ $10^{-4}$ for $CO_2^{2}$. Consequently, fatty acids production rates are usually limited by substrate availability.

The Membrane Biofilm Reactor (MBfR) overcomes all the challenges, because it delivers syngas directly to a biofilm that grows on the outer surface of a hollow-fiber membrane[4]. Here we use the MBfR with two different types of membranes, evaluating their effect in short chain fatty acids (SCFA) and medium chain fatty acids (MCFA) titers.

1.1. Methods 1.1.1. Set-Up

Figure 23:
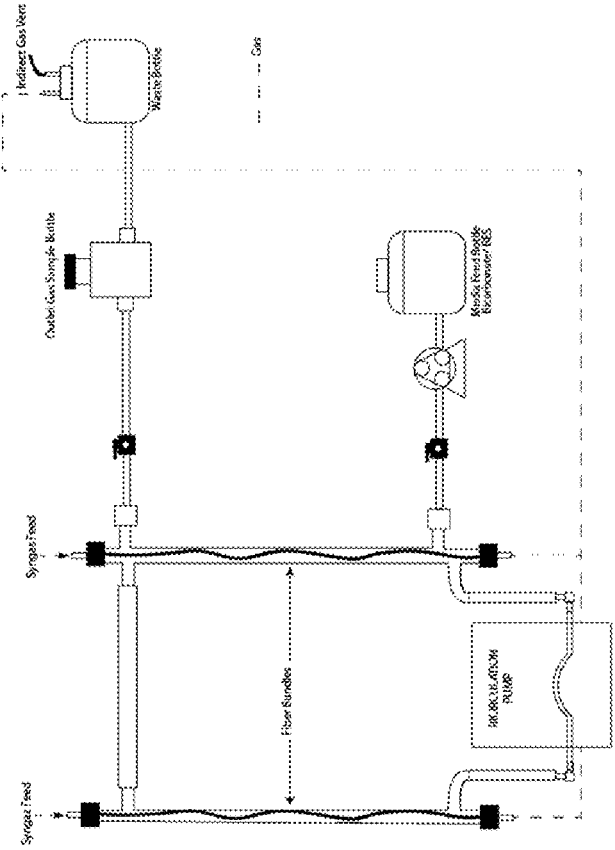
FIG. 23 shows a schematic of a Membrane Biofilm Reactor set-up used for syngas conversion to fatty acids in accordance with embodiments disclosed herein.

FIG. 23 shows the MBfR configuration[5] with two glass tubes connected with polytetrafluoroethylene (PTFE) tubing, stopcocks and fittings to avoid oxygen intrusion. The MBfR had a working volume of 70 mL. The system was continuously and completely mixed using a high recirculation rate (80 mL/min) with a peristaltic pump (Master Flex, model 7520-40, Cole-Parmer Instrument Company, U.S.A.).

Two types of hollow fibers were evaluated: one symmetric composite membrane with a non-porous layer of urethane polymers between two layers of polyethylene (Mitsubishi-Rayon®, MHF200TL) and one asymmetric composite membrane with a non-porous layer of polyimide and one porous layer of the same material. The bundle fibers were directly connected from one end to the gas supply and closed on the other end with a relief valve for flushing. Table 7 shows the specifications of the membranes used.

TABLE 7

Membrane properties

|  |  | Symmetric | Assymetric |
|---|---|---|---|
| Surface area | Am (m2) | 0.013006194 | 0.00021677 |
| Outer diameter | dm (m) | 0.00028 | 0.0003 |
| Inner diameter | zm (m) | 0.00005 | 0.00015 |
| Length of fiber | Lm (m) | 0.3 | 0.3 |
| Number of fibers in reactor | nm (−) | 60 | 1 |

The MBfRs was inoculated with 5 mL of waste activated sludge from a local wastewater treatment plant and 5 mL of an enriched acetogenic culture from a previous $H_2$-based MBfR. The biomass was allowed to attach to the fibers by leaving the reactor in batch mode with media as described in Delgado et al.[6], with 30 mM of sodium bicarbonate as buffer. After three days, the system was switched to continuous mode, allowing a hydraulic retention time of 24 hours by adjusting the flow to 0.05 mL/min. The media was fed with a peristaltic pump and PTFE tubing (Master Flex, model 7520-20, Cole-Parmer Instrument Company, U.S.A.). During continuous mode, the reactors were fed with a certified mixture of synthesis gas (30% $H_2$, 40% CO, 40% $CO_2$) at 2 psig through the hollow fibers.

1.2. Results

Figure 24:
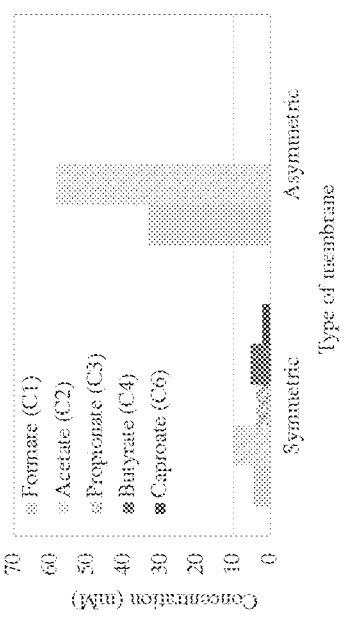
FIG. 24 shows a comparison in fatty acids production from syngas by an enriched biofilm using two different membranes for gas delivery.

FIG. 24 shows the effect of the type of membrane in the SCFA and MCFA titers achieved during steady-state in syngas-based MBfRs. Using the same pressure, the symmetric membrane constantly delivered a syngas flux of 19 $g/m^2$-d, considerably lower than the asymmetric membrane, which delivered 44 $g/m^2$-d. As a result, the asymmetric fiber exceeds by 6 times the formate and acetate concentration achieved in the symmetric fiber, but the symmetric fiber promoted chain elongation processes, obtaining up to caproate in the reactor. These results could be a consequence of the carbon limitation in the symmetric fiber, since $H_2$ is delivered faster than the other two gases. Even though the asymmetric fiber also delivers $H_2$ faster than the other two gases, its flux is high enough to avoid the gas as limiting factor and producing as much acetate and formate as the microorganisms are capable of.

Based on these results, it is beneficial for the selection of a membrane for acid production to consider if the goal is to have big production rates or rather promote chain elongation processes.

REFERENCES FOR EXAMPLE 4

1. Rittmann, B. E. & McCarty, P. L. *Environmental biotechnology: Principles and applications*. (2001).
2. Sander, R. Compilation of Henry's law constants (version 4.0) for water as solvent. *Atmos. Chem. Phys.* 15, 4399-4981 (2015).
3. Martin, K. J. & Nerenberg, R. The membrane biofilm reactor (MBfR) for water and wastewater treatment: Principles, applications, and recent developments. *Bioresour. Technol.* 122, 83-94 (2012).
4. Rittmann, B. E. The membrane biofilm reactor: the natural partnership of membranes and biofilm. *Water Sci. Technol.* 53, 219-225 (2006).
5. Zhou, C. et al. Uranium removal and microbial community in a H2-based membrane biofilm reactor. *Water Res.* 64, 255-264 (2014).
6. Delgado, A. G., Parameswaran, P., Fajardo-Williams, D., Halden, R. U. & Krajmalnik-Brown, R. Role of bicarbonate as a pH buffer and electron sink in microbial dechlorination of chloroethenes. *Microb. Cell Fact.* 11, (2012).

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A membrane carbonation system for cultivating a photoautotrophic organism in a photoautotrophic culture, the system comprising:

a membrane unit comprising a plurality of non-porous hollow-fiber membranes configured to be at least partially submerged in the photoautotrophic culture, wherein each of the non-porous hollow-fiber membranes comprises a lumen;

a valve fluidly coupled to an inlet of the membrane unit and configured to fluidly couple to a gas source comprising a mixture of gases comprising $CO_2$, the valve configured to control supply of the mixture of gases from the gas source to the lumen of each of the non-porous hollow-fiber membranes, wherein when the mixture of gases is present in the lumen of each of the non-porous hollow-fiber membranes, the $CO_2$ diffuses through the non-porous hollow-fiber membranes into the photoautotrophic culture; and a controller communicatively coupled to the valve, wherein the controller is configured to control the valve based on a pH of the photoautotrophic culture.

2. The membrane carbonation system of claim 1, further comprising a venting valve fluidly coupled to an outlet of the membrane unit, the venting valve configured to vent inert gases from the lumen of each of the non-porous hollow-fiber membranes.

3. The membrane carbonation system of claim 2, wherein the venting valve is configured to replace the inert gases within the non-porous hollow-fiber membranes with the mixture of gases when the pH of the photoautotrophic culture reaches a pH setpoint.

4. The membrane carbonation system of claim 2, wherein the venting valve is configured to vent the mixture of gases from the lumen of each of the non-porous hollow-fiber membranes at a relatively constant rate.

5. The membrane carbonation system of claim 1, further comprising a pH probe configured to be inserted into the photoautotrophic culture and to gather pH data regarding the pH of the photoautotrophic culture, wherein the controller is configured to receive the pH data from the pH probe and control the valve based on the pH data.

6. The membrane carbonation system of claim 1, wherein the mixture of gases includes a secondary gas that is more valuable when purified to a higher concentration as $CO_2$ is removed.

\* \* \* \* \*

38